(12) United States Patent
Guillonneau et al.

(10) Patent No.: US 10,105,425 B2
(45) Date of Patent: Oct. 23, 2018

(54) ISOLATED DONOR MHC-DERIVED PEPTIDE AND USES THEREOF

(71) Applicants: INSERM (INSTITUT NATIONAL DE LA SANTÉ ET DE LA RECHERCHE MÉDICALE), Paris (FR); UNIVERSITÉ DE NANTES, Nantes (FR)

(72) Inventors: Carole Guillonneau, Nantes (FR); Ignacio Anegon, Nantes (FR); Elodie Picarda, Nantes (FR)

(73) Assignees: Institut National de la Sante et de la Recherche Medicale (INSERM), Paris (FR); Universite de Nantes, Nantes (FR)

( * ) Notice: Subject to any disclaimer, the term of this patent is extended or adjusted under 35 U.S.C. 154(b) by 5 days.

(21) Appl. No.: 15/300,896

(22) PCT Filed: Apr. 1, 2015

(86) PCT No.: PCT/EP2015/057257
§ 371 (c)(1),
(2) Date: Sep. 30, 2016

(87) PCT Pub. No.: WO2015/150491
PCT Pub. Date: Oct. 8, 2015

(65) Prior Publication Data
US 2017/0021001 A1 Jan. 26, 2017

(30) Foreign Application Priority Data
Apr. 1, 2014 (EP) .................................. 14163081

(51) Int. Cl.
*C07K 14/74* (2006.01)
*A61K 39/00* (2006.01)
*C12N 5/0783* (2010.01)
*G01N 33/569* (2006.01)

(52) U.S. Cl.
CPC ...... *A61K 39/001* (2013.01); *C07K 14/70539* (2013.01); *C12N 5/0637* (2013.01); *G01N 33/56972* (2013.01); *A61K 2039/577* (2013.01); *C12N 2501/50* (2013.01); *C12N 2502/1121* (2013.01); *G01N 2333/70539* (2013.01); *G01N 2800/245* (2013.01); *G01N 2800/52* (2013.01)

(58) Field of Classification Search
None
See application file for complete search history.

(56) References Cited

U.S. PATENT DOCUMENTS

2009/0004213 A1* 1/2009 Singh ................. A61K 39/0011
424/185.1
2009/0317428 A1* 12/2009 Rammensee ...... C07K 14/4748
424/277.1

OTHER PUBLICATIONS

Van Denderen et al., Eur. J. Immunol. (2001) 31:1333-1339.*
Ballet C et al: "Indirect CD4+ TH1 response, antidoner antibodies and diffuse C4d graft deposits in long-term recipients conditioned by donor antigens priming.", American Journal of Transplantation: Official Journal of the American Society of Transplantation and the American Society of Transplant Surgeons Apr. 2009, vol. 9, No. 4, Apr. 2009, pp. 697-708.
Singh Harpreet et al: "Renal cancer treatment related human peptide sequence, SEQ ID 885", Database GENESEQ [Online], Jan. 1, 2009.
Michael Maria et al: "Regulatory T Cells in Allogeneic Stem Cell Transplantation", Clinical & Developmental Immunology, 2013.
Speir Jeffrey A et al: "Two different, highly exposed, bulged structures for an unusually long peptide bound to rat MHC class I RT1-Aa", Immunity, vol. 14, No. 1, Jan. 2001, pp. 81-92.
Picarda Elodie et al: "MHC-derived allopeptide activates TCR-biased CD8(+) Tregs and suppresses organ rejection", Journal of Clinical Investigation, vol. 124, No. 6, Jun. 2014, pp. 2497-2512.

* cited by examiner

*Primary Examiner* — Daniel C Gamett
(74) *Attorney, Agent, or Firm* — W&C IP

(57) ABSTRACT

The invention relates to an peptide derived from a polymorphic region of donor MHC class II molecules which induces tolerance and thus prevents transplant rejection in a patient in need thereof. The invention relates to an isolated peptide of 15 or 16 amino acids long that comprises or consists of the amino acid sequence: REEYARFDSDVGEYR (SEQ ID NO: 1) or a function-conservative variant for use as drug. The invention relates to an in vitro method for determining whether a transplanted patient is tolerant, comprising a step of determining the presence of $CD8^+CD45RC^{low}$ Tregs in a biological sample obtained from said transplanted patient, wherein the presence of $CD8^+CD45RC^{low}$ Tregs is indicative of tolerance.

Figure 1B:
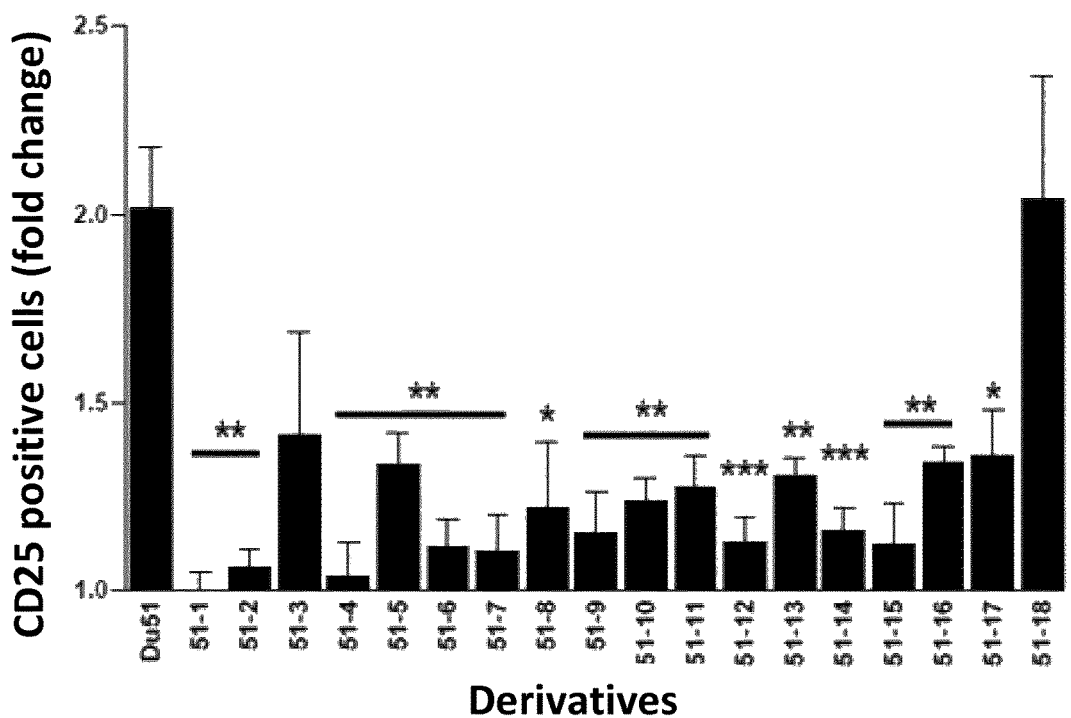

12 Claims, 6 Drawing Sheets
Specification includes a Sequence Listing.

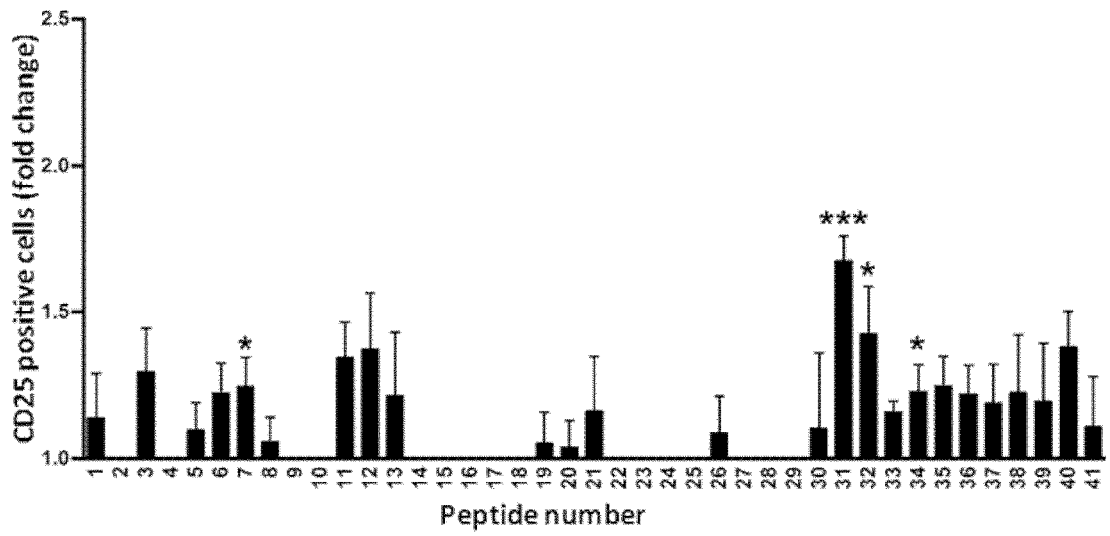
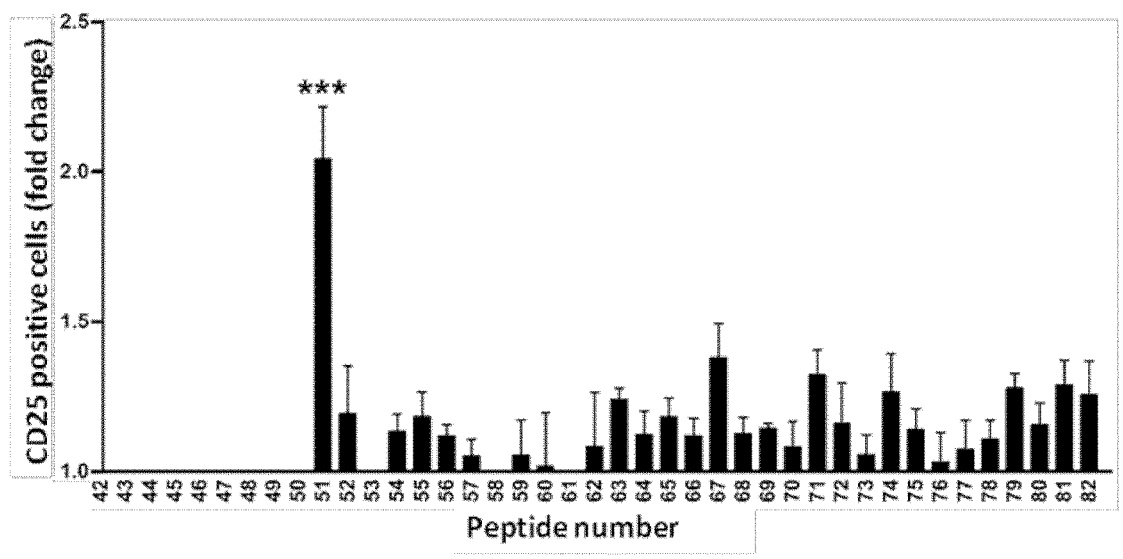
Figure 1A

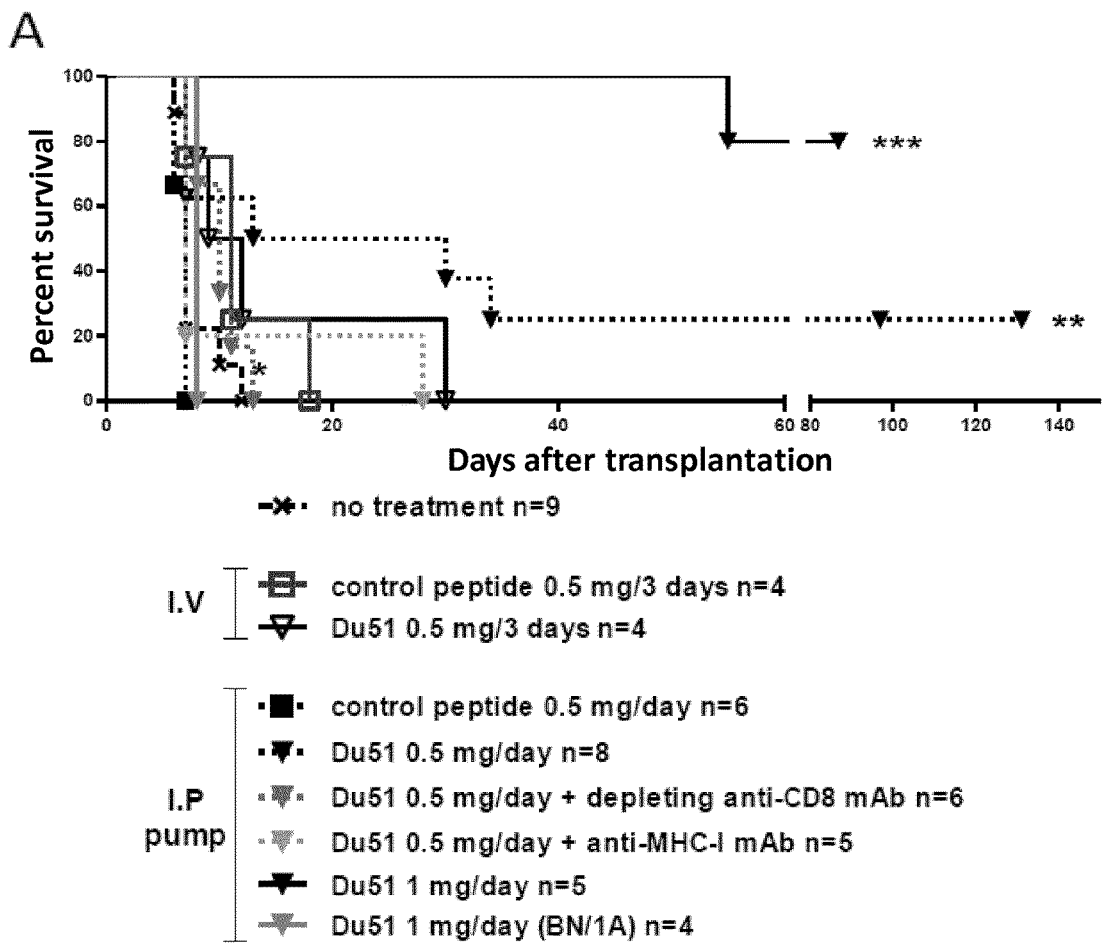
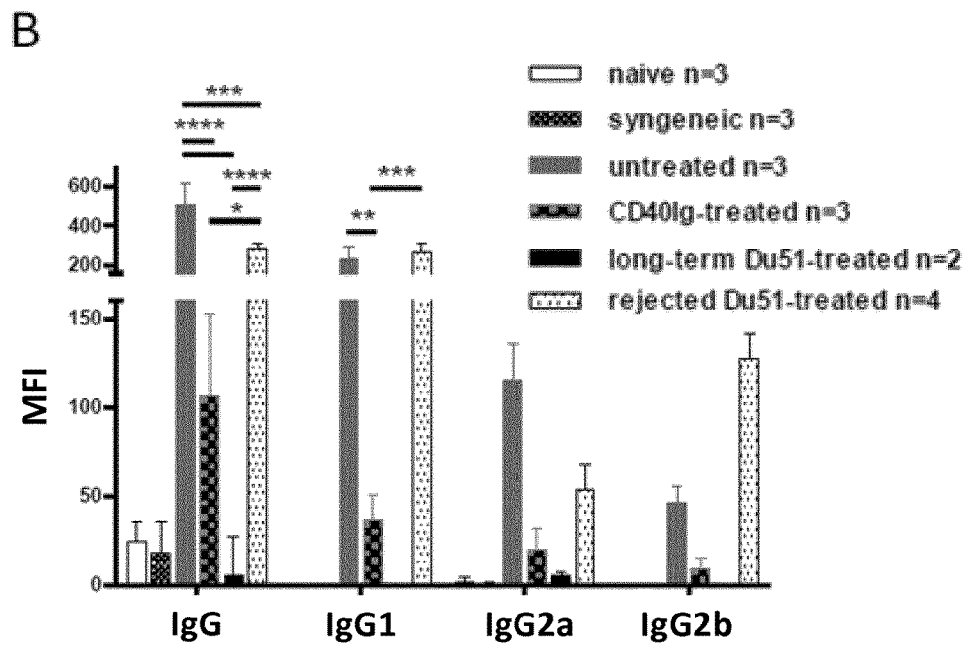
Figure 3A-B

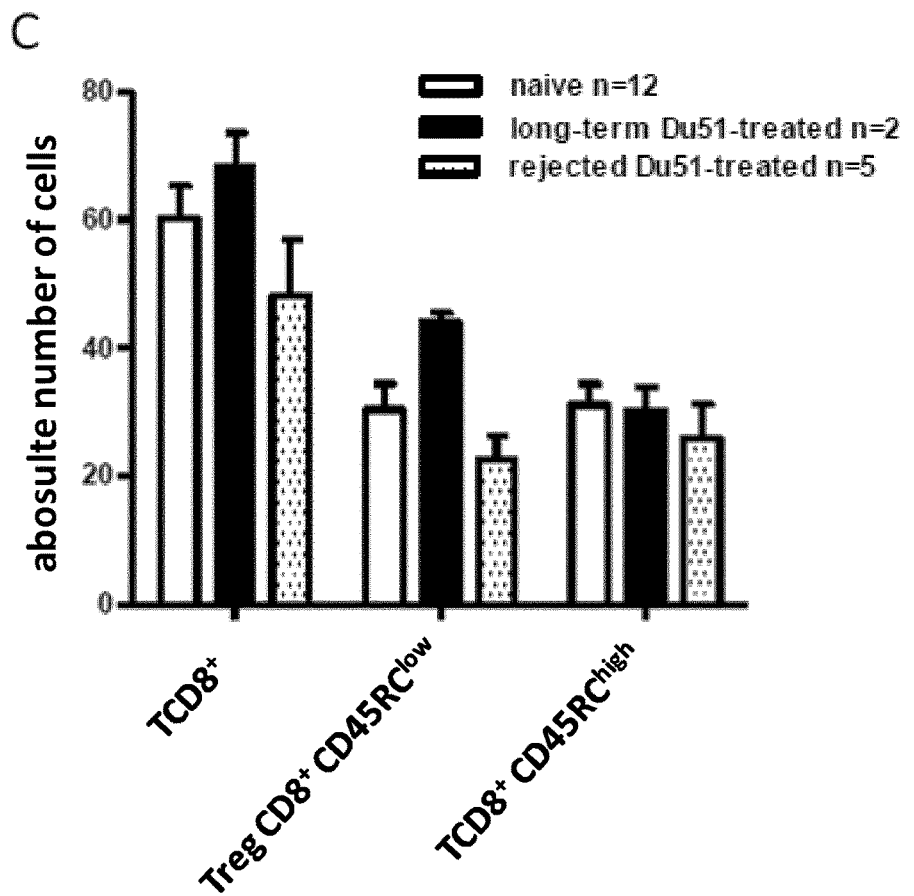
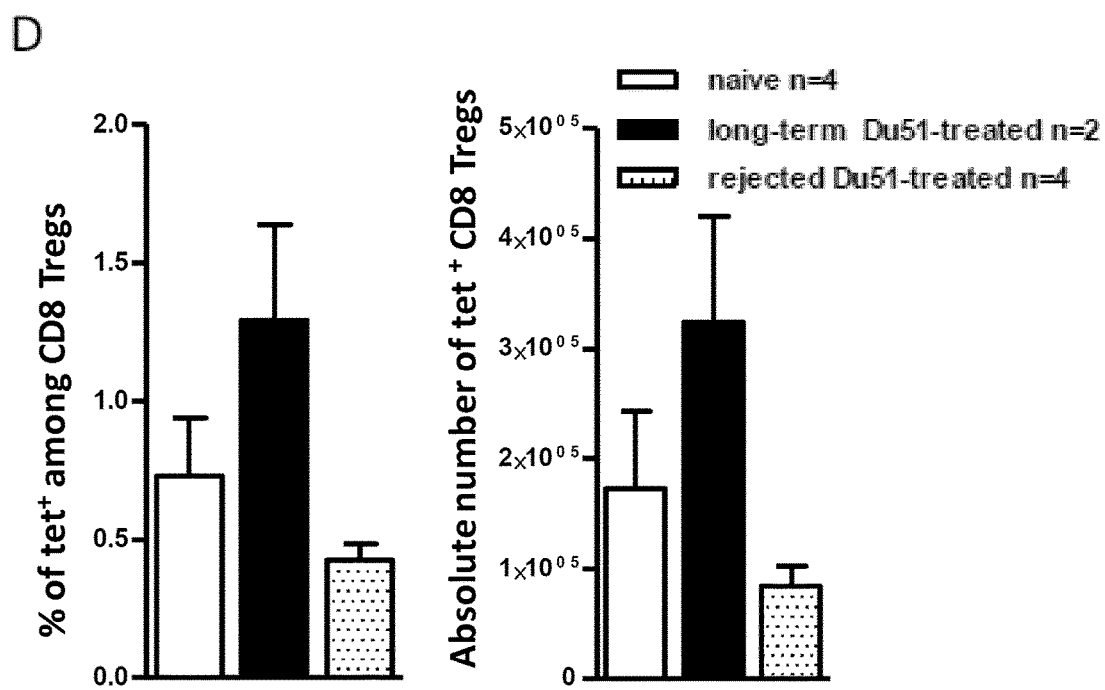
Figure 3C-D

SEQUENCE LISTING

<160> NUMBER OF SEQ ID NOS: 34

<210> SEQ ID NO 1
<211> LENGTH: 15
<212> TYPE: PRT
<213> ORGANISM: Artificial
<220> FEATURE:
<223> OTHER INFORMATION: Synthetic 15-mer peptide 51-18

<400> SEQUENCE: 1

Arg Glu Glu Tyr Ala Arg Phe Asp Ser Asp Val Gly Glu Tyr Arg
1               5                   10                  15

<210> SEQ ID NO 2
<211> LENGTH: 16
<212> TYPE: PRT
<213> ORGANISM: Artificial
<220> FEATURE:
<223> OTHER INFORMATION: Synthetic Dominant peptide Du51

<400> SEQUENCE: 2

Asn Arg Glu Glu Tyr Ala Arg Phe Asp Ser Asp Val Gly Glu Tyr Arg
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic Function-conservative variant of
      peptide 51-18

<400> SEQUENCE: 3

Arg Glu Glu Tyr Ala Arg Phe Asp Ser Asp Val Gly Glu Phe Arg
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic Function-conservative variant of
      peptide 51-18

<400> SEQUENCE: 4

Arg Glu Glu Tyr Val Arg Phe Asp Ser Asp Val Gly Glu Tyr Arg
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic Function-conservative variant of
      peptide 51-18

<400> SEQUENCE: 5

Gln Glu Glu Tyr Ala Arg Phe Asp Ser Asp Val Gly Glu Tyr Arg
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic Function-conservative variant of
      peptide 51-18

```
<400> SEQUENCE: 6

Arg Glu Glu Tyr Ala Arg Phe Asp Ser Asp Val Gly Val Tyr Arg
1               5                   10                  15

<210> SEQ ID NO 7
<211> LENGTH: 16
<212> TYPE: PRT
<213> ORGANISM: Artificial
<220> FEATURE:
<223> OTHER INFORMATION: Synthetic Function-conservative variant of
      peptide 51-18

<400> SEQUENCE: 7

Asn Arg Glu Glu Tyr Ala Arg Phe Asp Ser Asp Val Gly Glu Phe Arg
1               5                   10                  15

<210> SEQ ID NO 8
<211> LENGTH: 16
<212> TYPE: PRT
<213> ORGANISM: Artificial
<220> FEATURE:
<223> OTHER INFORMATION: Synthetic NQEEYARFDSDVGEYR

<400> SEQUENCE: 8

Asn Arg Glu Glu Tyr Val Arg Phe Asp Ser Asp Val Gly Glu Tyr Arg
1               5                   10                  15

<210> SEQ ID NO 9
<211> LENGTH: 16
<212> TYPE: PRT
<213> ORGANISM: Artificial
<220> FEATURE:
<223> OTHER INFORMATION: Synthetic Function-conservative variant of
      peptide 51-18

<400> SEQUENCE: 9

Asn Gln Glu Glu Tyr Ala Arg Phe Asp Ser Asp Val Gly Glu Tyr Arg
1               5                   10                  15

<210> SEQ ID NO 10
<211> LENGTH: 16
<212> TYPE: PRT
<213> ORGANISM: Artificial
<220> FEATURE:
<223> OTHER INFORMATION: Synthetic Function-conservative variant of
      peptide 51-18

<400> SEQUENCE: 10

Asn Arg Glu Glu Tyr Ala Arg Phe Asp Ser Asp Val Gly Val Tyr Arg
1               5                   10                  15

<210> SEQ ID NO 11
<211> LENGTH: 9
<212> TYPE: PRT
<213> ORGANISM: Artificial
<220> FEATURE:
<223> OTHER INFORMATION: Synthetic 9-mer peptide 51-1

<400> SEQUENCE: 11

Asn Arg Glu Glu Tyr Ala Arg Phe Asp
1               5

<210> SEQ ID NO 12
<211> LENGTH: 9
<212> TYPE: PRT
<213> ORGANISM: Artificial
<220> FEATURE:
```

<223> OTHER INFORMATION: Synthetic 9-mer peptide 51-2

<400> SEQUENCE: 12

Arg Glu Glu Tyr Ala Arg Phe Asp Ser
1               5

<210> SEQ ID NO 13
<211> LENGTH: 9
<212> TYPE: PRT
<213> ORGANISM: Artificial
<220> FEATURE:
<223> OTHER INFORMATION: Synthetic 9-mer peptide 51-3

<400> SEQUENCE: 13

Glu Glu Tyr Ala Arg Phe Asp Ser Asp
1               5

<210> SEQ ID NO 14
<211> LENGTH: 9
<212> TYPE: PRT
<213> ORGANISM: Artificial
<220> FEATURE:
<223> OTHER INFORMATION: Synthetic 9-mer peptide 51-4

<400> SEQUENCE: 14

Glu Tyr Ala Arg Phe Asp Ser Asp Val
1               5

<210> SEQ ID NO 15
<211> LENGTH: 9
<212> TYPE: PRT
<213> ORGANISM: Artificial
<220> FEATURE:
<223> OTHER INFORMATION: Synthetic 9-mer peptide 51-5

<400> SEQUENCE: 15

Tyr Ala Arg Phe Asp Ser Asp Val Gly
1               5

<210> SEQ ID NO 16
<211> LENGTH: 9
<212> TYPE: PRT
<213> ORGANISM: Artificial
<220> FEATURE:
<223> OTHER INFORMATION: Synthetic 9-mer peptide 51-6

<400> SEQUENCE: 16

Ala Arg Phe Asp Ser Asp Val Gly Glu
1               5

<210> SEQ ID NO 17
<211> LENGTH: 9
<212> TYPE: PRT
<213> ORGANISM: Artificial
<220> FEATURE:
<223> OTHER INFORMATION: Synthetic 9-mer peptide 51-7

<400> SEQUENCE: 17

Arg Phe Asp Ser Asp Val Gly Glu Tyr
1               5

<210> SEQ ID NO 18
<211> LENGTH: 9
<212> TYPE: PRT
<213> ORGANISM: Artificial
<220> FEATURE:
<223> OTHER INFORMATION: Synthetic 9-mer peptide 51-8

<400> SEQUENCE: 18

Phe Asp Ser Asp Val Gly Glu Tyr Arg
1               5

<210> SEQ ID NO 19
<211> LENGTH: 10
<212> TYPE: PRT
<213> ORGANISM: Artificial
<220> FEATURE:
<223> OTHER INFORMATION: Synthetic 10-mer peptide 51-9

<400> SEQUENCE: 19

Tyr Ala Arg Phe Asp Ser Asp Val Gly Glu
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic 10-mer peptide 51-10

<400> SEQUENCE: 20

Glu Tyr Ala Arg Phe Asp Ser Asp Val Gly
1               5                   10

<210> SEQ ID NO 21
<211> LENGTH: 11
<212> TYPE: PRT
<213> ORGANISM: Artificial
<220> FEATURE:
<223> OTHER INFORMATION: Synthetic 11-mer peptide 51-11

<400> SEQUENCE: 21

Glu Tyr Ala Arg Phe Asp Ser Asp Val Gly Glu
1               5                   10

<210> SEQ ID NO 22
<211> LENGTH: 11
<212> TYPE: PRT
<213> ORGANISM: Artificial
<220> FEATURE:
<223> OTHER INFORMATION: Synthetic 11-mer peptide 51-12

<400> SEQUENCE: 22

Tyr Ala Arg Phe Asp Ser Asp Val Gly Glu Tyr
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic 12-mer peptide 51-13

<400> SEQUENCE: 23

Tyr Ala Arg Phe Asp Ser Asp Val Gly Glu Tyr Arg
1               5                   10

<210> SEQ ID NO 24
<211> LENGTH: 12
<212> TYPE: PRT
<213> ORGANISM: Artificial
<220> FEATURE:
<223> OTHER INFORMATION: Synthetic 12-mer peptide 51-14

```
<400> SEQUENCE: 24

Glu Tyr Ala Arg Phe Asp Ser Asp Val Gly Glu Tyr
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic 12-mer peptide 51-15

<400> SEQUENCE: 25

Glu Glu Tyr Ala Arg Phe Asp Ser Asp Val Gly Glu
1               5                   10

<210> SEQ ID NO 26
<211> LENGTH: 13
<212> TYPE: PRT
<213> ORGANISM: Artificial
<220> FEATURE:
<223> OTHER INFORMATION: Synthetic 13-mer peptide 51-16

<400> SEQUENCE: 26

Glu Glu Tyr Ala Arg Phe Asp Ser Asp Val Gly Glu Tyr
1               5                   10

<210> SEQ ID NO 27
<211> LENGTH: 14
<212> TYPE: PRT
<213> ORGANISM: Artificial
<220> FEATURE:
<223> OTHER INFORMATION: Synthetic 14-mer peptide 51-17

<400> SEQUENCE: 27

Glu Glu Tyr Ala Arg Phe Asp Ser Asp Val Gly Glu Tyr Arg
1               5                   10

<210> SEQ ID NO 28
<211> LENGTH: 40
<212> TYPE: PRT
<213> ORGANISM: Artificial
<220> FEATURE:
<223> OTHER INFORMATION: Synthetic Peptide of 40 amino acids derived
      from a MHC class II molecule

<400> SEQUENCE: 28

Arg Leu Leu Ala Arg Leu Ile Tyr Asn Arg Glu Glu Tyr Ala Arg Phe
1               5                   10                  15

Asp Ser Asp Val Gly Glu Tyr Arg Ala Val Thr Glu Leu Gly Arg Pro
            20                  25                  30

Ser Ala Glu Tyr Arg Asn Lys Gln
        35                  40

<210> SEQ ID NO 29
<211> LENGTH: 15
<212> TYPE: PRT
<213> ORGANISM: Artificial
<220> FEATURE:
<223> OTHER INFORMATION: Synthetic Function-conservative variant of
      peptide 51-18

<400> SEQUENCE: 29

Gln Glu Glu Tyr Val Arg Phe Asp Ser Asp Val Gly Glu Tyr Arg
1               5                   10                  15
```

```
<210> SEQ ID NO 30
<211> LENGTH: 16
<212> TYPE: PRT
<213> ORGANISM: Artificial
<220> FEATURE:
<223> OTHER INFORMATION: Synthetic Function-conservative variant of
      peptide 51-18

<400> SEQUENCE: 30

Asn Arg Glu Glu Phe Val Arg Phe Asp Ser Asp Val Gly Glu Phe Arg
1               5                   10                  15

<210> SEQ ID NO 31
<211> LENGTH: 15
<212> TYPE: PRT
<213> ORGANISM: Artificial
<220> FEATURE:
<223> OTHER INFORMATION: Synthetic Function-conservative variant of
      peptide 51-18

<400> SEQUENCE: 31

Arg Glu Glu Phe Val Arg Phe Asp Ser Asp Val Gly Glu Phe Arg
1               5                   10                  15

<210> SEQ ID NO 32
<211> LENGTH: 16
<212> TYPE: PRT
<213> ORGANISM: Artificial
<220> FEATURE:
<223> OTHER INFORMATION: Synthetic Function-conservative variant of
      peptide 51-18

<400> SEQUENCE: 32

His Gln Glu Glu Tyr Val Arg Phe Asp Ser Asp Val Gly Glu Tyr Arg
1               5                   10                  15

<210> SEQ ID NO 33
<211> LENGTH: 17
<212> TYPE: PRT
<213> ORGANISM: Artificial
<220> FEATURE:
<223> OTHER INFORMATION: Synthetic Function-conservative variant of
      peptide 51-18

<400> SEQUENCE: 33

His Gln Glu Glu Tyr Val Arg Phe Asp Ser Asp Val Gly Glu Tyr Arg
1               5                   10                  15

Ala

<210> SEQ ID NO 34
<211> LENGTH: 18
<212> TYPE: PRT
<213> ORGANISM: Artificial
<220> FEATURE:
<223> OTHER INFORMATION: Synthetic Function-conservative variant of
      peptide 51-18

<400> SEQUENCE: 34

His Gln Glu Glu Tyr Val Arg Phe Asp Ser Asp Val Gly Glu Tyr Arg
1               5                   10                  15

Ala Val
```

ISOLATED DONOR MHC-DERIVED PEPTIDE AND USES THEREOF

FIELD OF THE INVENTION

The invention is in the field of immunotherapy.

More particularly, the invention relates to an isolated peptide derived from a polymorphic region of donor MHC class II molecules which induces tolerance and thus prevents transplant rejection in a patient in need thereof.

BACKGROUND OF THE INVENTION

Allogeneic human to human transplant remains the best treatment to replace organs that have failed following disease. The incompatibility between the molecules of the major histocompatibility complex (MHC) of the recipient and donor cells is the main barrier to long-term success of organ transplantation. The induction of tolerance to the allograft has become a major objective and certain tolerance strategies are beginning to be applied clinically (1). Different populations of Tregs have been described as being capable of inducing tolerance to allogeneic organs. Most of these Tregs are CD4$^+$ Tregs, while CD8$^+$ Tregs are less well defined (2).

It has been previously described that costimulation blockade of CD40-CD40L interaction, one of the most efficient strategies to prolong organ allograft survival (3), induces CD8$^+$CD45RC$^{low}$ Tregs cells (called CD8$^+$CD40Ig Tregs) with potent suppressive capacity (2, 4-6). It has been showed that donor-specific CD8$^+$CD40Ig Tregs but not natural CD8$^+$CD45RC$^{low}$ Tregs transferred tolerance to naive transplant recipients. In addition, these cells acted in an unusual way as allograft survival was dependent on their secretion of interferon-γ (IFNγ) to enhance indoleamine 2,3-dioxygenase (IDO) expression by dendritic cells (DC) and graft endothelial cells (EC) (5). It has also been recently showed that the suppressive activity of the CD8$^+$CD40Ig Tregs was mainly performed in the presence of plasmacytoid DCs (pDCs) and that fibrinogen-like protein 2 (FGL2) was involved in the suppression (6).

The requirement for a TCR interaction in the shaping of the regulatory T cell population is an active and ongoing debate (2, 7). Some studies suggest that TCR specificity and diversity is critical for in vivo function and potency of CD8$^+$ Tregs (2, 7-13). Different models for CD4$^+$ Tregs have shown that antigen-specific Tregs are more potent suppressor than unrestricted Treg cells (2, 14). It is also known for CD4$^+$ Tregs that TCR diversity is critical for thymic selection and differentiation and its impact on Treg generation and function has been recently described (15). High-throughput sequencing has shown that naive Tregs with high TCR diversity expand more efficiently, are more adaptable and more efficient in suppressing Graft versus Host Disease (GVHD) upon adoptive transfer than TCR restricted Tregs (13, 16). Using Immunoscope®, it has been previously demonstrated that CD8$^+$CD40Ig Tregs accumulated a biased repertoire toward the Vβ11 element (5), suggesting the possibility of a clonal expansion. To date, little is known on the recognition features of this Treg population, or of CD8$^+$ Treg populations in general. The exact role of TCR/MHC/peptide interaction in Treg activity thus remains a topic of debate.

Moreover, there is still a great need for providing efficient therapeutic strategies based on Treg-mediated suppression of immune response against the transplant (such as donor-specific antibodies which are associated with antibody-mediated rejection) thus avoiding the need to use non specific immunosuppressive drugs which have the drawbacks to increase the attack rate of opportunistic diseases (e.g. bacterial, viral or fungal infections) and increase the mortality of transplanted patients.

SUMMARY OF THE INVENTION

In a first aspect, the invention relates to an isolated peptide of length ranging between 15 and 40 amino acids which is derived from a MHC class II molecule that comprises the amino acid sequence: REEYARFDSDVGEYR (SEQ ID NO: 1) or a function-conservative variant thereof.

In a second aspect, the invention relates to a MHC/peptide multimer comprising a peptide of length ranging between 15 and 25 amino acids that comprises or consists of the amino acid sequence: REEYARFDSDVGEYR (SEQ ID NO: 1) or a function-conservative variant thereof.

In a third aspect, the invention relates to an in vitro or ex vivo method for generating a population of CD8$^+$ CD45RC$^{low}$ Tregs, comprising a step of culturing a population of CD8$^+$ Tregs with a culture medium comprising an isolated peptide according to the invention in the presence of a population of plasmacytoid dendritic cells.

In a fourth aspect, the invention relates to an in vitro or ex vivo method for generating a population of CD8$^+$ CD45RC$^{low}$ Tregs, comprising a step of culturing a population of CD8+ Tregs with a culture medium comprising a MHC/peptide multimer according to the invention.

In a fifth aspect, the invention relates to an isolated peptide of the invention or a MHC/peptide multimer for use as drug, for use in inducing tolerance in a patient in need thereof, and for use in preventing or reducing transplant rejection in a patient in need thereof.

In a sixth aspect, the invention relates to a pharmaceutical composition comprising:
  a) an isolated peptide of the invention; or
  b) an acid nucleic encoding a peptide of the invention; or
  c) a vector comprising such nucleic acid; or
  d) a host cell comprising such expression vector; or
  e) a MHC/peptide multimer of the invention, or
  f) an antigen-presenting cell comprising a complex MHC molecule and a peptide of the invention; or
  g) a T lymphocyte that recognizes specifically the peptide of the invention;
  and a pharmaceutically acceptable carrier.

In a seventh aspect, the invention relates to an in vitro method for determining whether a transplanted patient (recipient) is tolerant, comprising a step of determining the presence of CD8+CD45RClow Tregs in a biological sample obtained from said transplanted patient, wherein the presence of CD8+CD45RClow Tregs is indicative of tolerance.

DETAILED DESCRIPTION OF THE INVENTION

The inventors have investigated whether CD8$^+$CD40Ig Tregs' TCR fine specificity influences Treg function and allograft survival and have thus demonstrated for the first time in transplantation that induced CD8$^+$CD40Ig Tregs recognized a dominant peptide (called Du51) derived from a polymorphic region of donor MHC class II molecules. This peptide expanded CD8$^+$ Tregs in the presence of pDCs, at least ex vivo, and induced tolerance in naive transplanted recipients without additional treatment.

In addition, the inventors generated a specific tetramer and demonstrated ex vivo and in vivo the dominant tolerance exerted by antigen-specific CD8+CD40Ig Tregs. Finally, they demonstrated that this peptide was recognized by Tregs expressing Vβ11 and Vβ18-specific TCRs. These TCRs comprised a private but restricted Vβ11 repertoire in the spleen and graft, but a private and diverse Vβ18 repertoire in the spleen and a more restricted Vβ18 repertoire in the graft, that ensure efficient suppression of alloreactive immune responses.

Peptides of the Invention

A first aspect of the invention relates to an isolated peptide of length ranging between 15 and 40 amino acids which is derived from a MHC class II molecule that comprises the amino acid sequence: REEYARFDSDVGEYR (SEQ ID NO: 1) (also called herein 51-18) or a function-conservative variant thereof.

In one embodiment of the invention, the peptide is an isolated peptide of length ranging between 15 and 40 amino acids which is derived from a MHC class II molecule that comprises the amino acid sequence: REEYARFDSD-VGEYR (SEQ ID NO: 1) or a function-conservative variant thereof with the exclusion of the following peptides:

NREEYARFDSDVGEYR; (SEQ ID NO: 2)

QEEYVRFDSDVGEYR; (SEQ ID NO: 29)

NREEFVRFDSDVGEFR; (SEQ ID NO: 30)

REEFVRFDSDVGEFR; (SEQ ID NO: 31)

HQEEYVRFDSDVGEYR; (SEQ ID NO: 32)

HQEEYVRFDSDVGEYRA; (SEQ ID NO: 33)
and

HQEEYVRFDSDVGEYRAV. (SEQ ID NO: 34)

As used herein, the term "function-conservative variant" refers to those comprise at least 70% identity with a peptide of reference (such as SEQ ID NO: 1), even more preferably at least 75%, 80%, 85%, 90%, 95%, 96%, 97%, 98%, 99%, 99.5% or 99.9%, and is still able to induce tolerance and thus prevent organ rejection in substantially the same way as a peptide of reference (such as SEQ ID NO: 1 (51-18)).

In one embodiment of the invention, said peptide is derived from a polymorphic region of a donor MHC class II molecule.

In a particular embodiment, said peptide consists of the amino acid sequence: RLLARLIYNREEYARFDSDVGEY-RAVTELGRPSAEYRNKQ (SEQ ID NO: 28) or a function-conservative variant thereof.

In one embodiment, the peptide of the invention comprises at least 70% identity with the peptide of SEQ ID NO: 28, even more preferably at least 75%, 80%, 85%, 90%, 95%, 96%, 97%, 98%, 99%, 99.5% or 99.9%, and is still able to induce tolerance and thus prevent organ rejection in substantially the same way as the peptide of SEQ ID NO: 28.

In one embodiment of the invention, said peptide comprises at most 15, 16, 17, 18, 19, 20, 21, 22, 23, 24, 25, 26, 27, 28, 29, 30, 31, 32, 33, 34, 35, 36, 37, 38, 39 or 40 amino acids.

In a particular embodiment of the invention, the peptide is an isolated peptide of 15 or 16 amino acids long that comprises or consists of the amino acid sequence: REE-YARFDSDVGEYR (SEQ ID NO: 1) (also called herein 51-18) or a function-conservative variant thereof.

In a particular embodiment of the invention, the peptide is an isolated peptide of 15 or 16 amino acids long that comprises or consists of the amino acid sequence: REE-YARFDSDVGEYR (SEQ ID NO: 1) (also called herein 51-18) or a function-conservative variant thereof with the proviso that said variant is not a peptide consisting of the amino acid sequence: NREEYARFDSDVGEYR (SEQ ID NO: 2) (also called herein Du51).

As used herein, the term "peptide" refers to a polymer of amino acid residues joined by peptide bonds, whether produced naturally or synthetically, having no specific length. The term peptide does not exclude post-translational modifications that include but are not limited to phosphorylation, acetylation, glycosylation and the like. The term also applies to amino acid polymers in which one or more amino acid residue is an artificial chemical mimetic of a corresponding naturally occurring amino acid, as well as to naturally occurring amino acid polymers and non-naturally occurring amino acid polymer.

By an "isolated" peptide, it is intended that the peptide is essentially free from contaminating cellular components, such as carbohydrate, lipid, or other proteinaceous impurities associated with the polypeptide in nature. Typically, a preparation of isolated peptide contains the peptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated peptide is by the appearance of a single band following SDS-polyacrylamide gel electrophoresis of the protein preparation and Coomassie Brilliant Blue staining of the gel. Alternatively, other analytical chemistry techniques such as high performance liquid chromatography (HPLC) or mass spectrometry (MS) may also be used to determine purity. A peptide that is the predominant specie present in a preparation is substantially purified.

The invention also encompasses peptides that are function-conservative variants of the peptide comprising SEQ ID NO: 1 as described here above.

In one embodiment, the peptide of the invention comprises at least 70% identity with the peptide of SEQ ID NO: 1, even more preferably at least 75%, 80%, 85%, 90%, 95%, 96%, 97%, 98%, 99%, 99.5% or 99.9%, and is still able to induce tolerance and thus prevent organ rejection in substantially the same way as the peptide of SEQ ID NO: 1.

By a polypeptide having an amino acid sequence at least, for example, 95% "identical" to a query amino acid sequence of the invention, it is intended that the amino acid sequence of the subject peptide is identical to the query sequence except that the subject peptide sequence may include up to five amino acid alterations per each 100 amino acids of the query amino acid sequence. In other words, to obtain a peptide having an amino acid sequence at least 95% identical to a query amino acid sequence, up to 5% (5 of 100) of the amino acid residues in the subject sequence may be inserted, deleted, or substituted with another amino acid.

In the frame of the application, the percentage of identity is calculated using a global alignment (i.e., the two sequences are compared over their entire length). Methods for comparing the identity and homology of two or more sequences are well known in the art. The "needle" program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

In one embodiment, the peptide according to the invention may differ from 1, 2, 3 or 4 amino acids to the SEQ ID NO: 1 or SEQ ID NO: 2 (Du51).

Such a peptide may for example only comprise substitutions compared to the reference sequence. The substitutions preferably correspond to conservative substitutions as indicated in the table below:

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

Typically, the invention encompasses peptides substantially identical to the peptide consisting of SEQ ID NO: 1 (51-18) or SEQ ID NO: 2 (Du51) in which one or more residues have been conservatively substituted with a functionally similar residue and which displays the functional aspects of the peptides consisting of SEQ ID NO: 1 (51-18) or SEQ ID NO: 2 (Du51) as described here below, i.e. being still able to induce tolerance and thus prevent organ rejection in substantially the same way as a peptide consisting of the given amino acid sequence (e.g. the peptides 51-18 or Du51).

The term "conservative substitution" also includes the use of a chemically derivatized residue in place of a non-derivatized residue. "Chemical derivative" refers to a peptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Chemical derivatives also include peptides that contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The term "conservative substitution" also includes the use of non natural amino acids aimed to control and stabilize peptides or proteins secondary structures. These non natural amino acids are chemically modified amino acids such as prolinoamino acids, beta-amino acids, N-methylamino acids, cyclopropylamino acids, alpha,alpha-substituted amino acids as describe here below. These non natural amino acids may include also fluorinated, chlorinated, brominated- or iodinated modified amino acids.

To verify whether the newly generated peptides induce the same biological properties than the initially characterized peptides 51-18 or Du51, an analysis of $CD8^+$ $CD45RC^{low}$ Treg activation and/or an analysis of tolerance induction after in vivo peptide infusion (such as described in the section EXAMPLE) may be performed with each peptide. Additionally, a time-course and a dose-response performed in a model of allograft will determine the optimal conditions for each peptide.

In one embodiment, the peptide consists of the amino acid sequence selected from the group consisting of:

```
                                      (SEQ ID NO: 3)
        REEYARFDSDVGEFR, (SEQ ID NO: 4)
        REEYVRFDSDVGEYR, (SEQ ID NO: 5)
        QEEYARFDSDVGEYR,
        or (SEQ ID NO: 6)
        REEYARFDSDVGVYR.
```

In one embodiment, the peptide having the amino acid sequence: REEYARFDSDVGEYR (SEQ ID NO: 1) bears an asparagine (N) at the N-terminus.

In a preferred embodiment, the peptide consists of the amino acid sequence selected from the group consisting of:

```
                                      (SEQ ID NO: 7)
        NREEYARFDSDVGEFR, (SEQ ID NO: 8)
        NREEYVRFDSDVGEYR, (SEQ ID NO: 9)
        NQEEYARFDSDVGEYR,
        or (SEQ ID NO: 10)
        NREEYARFDSDVGVYR.
```

According to the invention, the peptides of the invention may be produced by conventional automated peptide synthesis methods or by recombinant expression. General principles for designing and making proteins are well known to those of skill in the art.

Peptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. Peptides of the invention may also be synthesized by solid-phase technology employing an exemplary peptide synthesizer such as a Model 433A from Applied Biosystems Inc. The purity of any given peptide; generated through automated peptide synthesis or through recombinant methods may be determined using reverse phase HPLC analysis. Chemical authenticity of each peptide may be established by any method well known to those of skill in the art. As an alternative to automated peptide synthesis, recombinant DNA technology may be employed wherein a nucleotide sequence which encodes a peptide of choice is inserted into an expression vector, transformed or transfected into an appropriate host cell and cultivated under conditions suitable for expression as described herein below. Recombinant methods are especially preferred for producing longer peptides (polypeptides).

Nucleic Acids, Vectors and Recombinant Host Cells

Alternatively, a nucleic acid encoding a peptide of the invention (such as the peptide shown in SEQ ID NO: 1), a vector comprising such nucleic acid or a host cell comprising such expression vector are also of interest within the context of the invention.

In one embodiment, the peptide consists of an amino acid sequence described above.

Nucleic acids of the invention may be produced by any technique known per se in the art, such as, without limitation, any chemical, biological, genetic or enzymatic technique, either alone or in combination(s).

In its broadest sense, a "vector" is any vehicle capable of facilitating the transfer of a nucleic acid to the cells In general, the vectors useful in the invention include, but are not limited to, plasmids, phagemids, viruses, other vehicles derived from viral or bacterial sources that have been manipulated by the insertion or incorporation of the nucleic acid sequences of interest. Viral vectors are a preferred type of vector and include, but are not limited to nucleic acid sequences from the following viruses: retrovirus, such as moloney murine leukemia virus, harvey murine sarcoma virus, murine mammary tumor virus, and mouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired peptides, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, 5V40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, and microencapsulation.

According to the invention, examples of host cells that may be used are antigen-presenting cells (APC) such as human dendritic cells or monocytes (particularly those obtained from the patient to be treated).

The means by which the vector carrying the gene may be introduced into the cells include, but are not limited to, microinjection, electroporation, transduction, or transfection using DEAE-dextran, lipofection, calcium phosphate or other procedures known to one skilled in the art.

MHC/Peptide Multimers

Another aspect of the invention is a MHC/peptide multimer comprising a peptide of length ranging between 15 and 25 amino acids that comprises or consists of the amino acid sequence: REEYARFDSDVGEYR (SEQ ID NO: 1) (also called herein 51-18) or a function-conservative variant thereof as described here above.

In one embodiment of the invention, said peptide comprises at most 15, 16, 17, 18, 19, 20, 21, 22, 23, 24 or 25 amino acids.

In a particular embodiment, said MHC/peptide multimer comprises a peptide of 15 or 16 amino acids long that comprises or consists of the amino acid sequence: REEYARFDSDVGEYR (SEQ ID NO: 1) (also called herein 51-18) or a function-conservative variant thereof as described here above.

As used herein, the term "MHC/peptide multimer" refers to a stable multimeric complex composed of major histocompatibility complex (MHC) protein subunits loaded with a peptide of the invention. According to the invention, said MHC/peptide multimer (also called herein MHC/peptide complex) include, but are not limited to, a MHC/peptide dimer, trimer, tetramer or pentamer.

The term "Major Histocompatibility Complex" (MHC) is a generic designation meant to encompass the histo-compatibility antigen systems described in different species including the human leucocyte antigens (HLA).

In one embodiment of the invention, the MHC/peptide multimer is a MHC class I/peptide multimer.

In a particular embodiment of the invention, said MHC/peptide multimer is a rat MHC RT1.A$^a$/peptide multimer. It should be further noted that nonclassical rat MHC class I molecules are also encompassed within the context of the invention.

In another particular embodiment, the MHC/peptide multimer is a HLA corresponding to MHC class I/peptide multimer.

In humans there are three major different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*11 are examples of different MHC class I alleles that can be expressed from these loci.

It should be further noted that nonclassical human MHC class I molecules such as HLA-E (functional homolog in mice is called Qa-1b) and MICA/B molecules are also encompassed within the context of the invention.

Accordingly, the MHC/peptide multimer is a HLA/peptide multimer selected from the group consisting of HLA-A/peptide multimer, HLA-B/peptide multimer, HLA-C/peptide multimer, HLA-E/peptide multimer, MICA/peptide multimer and MICB/peptide multimer.

In one embodiment, said isolated peptide is selected from the group consisting of:

```
                            (SEQ ID NO: 1)
REEYARFDSDVGEYR;

(SEQ ID NO: 2)
NREEYARFDSDVGEYR;

(SEQ ID NO: 3)
REEYARFDSDVGEFR;

(SEQ ID NO: 4)
REEYVRFDSDVGEYR;

(SEQ ID NO: 5)
QEEYARFDSDVGEYR;

(SEQ ID NO: 6)
REEYARFDSDVGVYR;

(SEQ ID NO: 7)
NREEYARFDSDVGEFR;

(SEQ ID NO: 8)
NREEYVRFDSDVGEYR;

(SEQ ID NO: 9)
NQEEYARFDSDVGEYR
or
                            (SEQ ID NO: 10)
NREEYARFDSDVGVYR.
```

Methods for obtaining MHC/peptide tetramers are described in WO96/26962 and WO01/18053, which are incorporated by reference.

In one embodiment of the invention, said MHC/peptide multimer can be used to visualise T cell populations that are specific for the MHC class I RT1.A$^a$/peptide complex or a HLAs corresponding to MHC class I/peptide complex as described here above.

The MHC/peptide multimer may be a multimer where the heavy chain of the MHC is biotinylated, which allows combination as a tetramer with streptavidine. Such MHC-peptide tetramer has an increased avidity for the appropriate TCR-carrier T lymphocytes and can therefore be used to visualize reactive populations by immunofluorescence.

In another embodiment of the invention, said MHC/peptide multimer can be used for the detection and/or isolation by screening (in flow cytometry or by immunomagnetic screening) of T cell populations that are specific for a MHC/peptide complex as described here above.

In a particular embodiment of the invention, a MHC class I RT1.A$^a$/peptide multimer or a HLA corresponding to MHC class I/peptide multimer can be used for the detection and/or isolation by screening (in flow cytometry or by immunomagnetic screening) of T cell populations that are specific for said MHC class I RT1.A$^a$/peptide complex or said HLA corresponding to MHC class I/peptide multimer as described here above.

Another aspect of the invention is beads, microspheres or nanoparticles coated with a MHC/peptide multimer as described here above.

Antigen Presenting Cells and Uses Thereof

Another aspect of the invention is a peptide-presenting cell comprising a MHC/peptide multimer of the invention as described here above.

In one embodiment of the invention, said multimer MHC/peptide is a MHC class I RT1.A$^a$/peptide multimer.

In another particular embodiment, the MHC/peptide multimer is a HLA corresponding to MHC class I/peptide multimer as defined above.

Accordingly, the MHC/peptide multimer is a HLA/peptide multimer selected from the group consisting of HLA-A/peptide multimer, HLA-B/peptide multimer, HLA-C/peptide multimer, HLA-E/peptide multimer, MICA/peptide multimer and MICB/peptide multimer.

In one embodiment, said peptide is selected from the group consisting of:

```
                            (SEQ ID NO: 1)
REEYARFDSDVGEYR;

(SEQ ID NO: 2)
NREEYARFDSDVGEYR;

(SEQ ID NO: 3)
REEYARFDSDVGEFR;

(SEQ ID NO: 4)
REEYVRFDSDVGEYR;

(SEQ ID NO: 5)
QEEYARFDSDVGEYR;

(SEQ ID NO: 6)
REEYARFDSDVGVYR;

(SEQ ID NO: 7)
NREEYARFDSDVGEFR;

(SEQ ID NO: 8)
NREEYVRFDSDVGEYR;

(SEQ ID NO: 9)
NQEEYARFDSDVGEYR
or
                            (SEQ ID NO: 10)
NREEYARFDSDVGVYR.
```

In one embodiment of the invention, said antigen presenting cell is derived from the patient to be treated.

As used herein, the terms "antigen-presenting cell" (APC) also called herein "peptide-presenting cell" are used interchangeably and refer to a class of immune cells capable of internalizing and processing an antigen, so that antigenic determinants are presented on the surface of the cell as MHC-associated complexes, in a manner capable of being recognized by the immune system (e. g., MHC class I restricted cytotoxic T lymphocytes and/or MHC class II restricted helper T lymphocytes). The two requisite properties that allow a cell to function as an APC are the ability to process endocytosed antigens and the expression of MHC gene products. Examples of APC include dendritic cells (DC), mononuclear phagocytes (e. g. macrophages), B lymphocytes, Langerhans cells of the skin and, in humans, endothelial cells.

In one embodiment of the invention, said APC is a plasmacytoid dendritic cell (pDC).

As used herein, the term "plasmacytoid dendritic cells" (pDC) refers to innate immune cells that circulate in the blood and are found in peripheral lymphoid organs. They constitute a group of cells belonging to the peripheral blood mononuclear cells (PBMC) group. Human pDCs typically express the surface markers IL-3 receptor a chain (IL-3Ra, CD123), BDCA-2 (CD303) and BDCA-4 (CD304), but do not express CD11c or CD14, which distinguishes them from conventional dendritic cells or monocytes.

In one embodiment of the invention, said pDC is a mature pDC. Mature pDCs typically express the surface markers HLA-DR, CD86 and produce large amount of IFNalpha and IFNbeta.

In order to prepare such APCs of the invention, cells having an antigen-presenting ability are isolated from the patient to be treated, and pulsed ex vivo with a peptide of the invention to form a complex with the MHC molecule.

In case dendritic cells are used, the APC of the invention can be prepared as follows. Lymphocytes are isolated from peripheral blood of the patient to be treated by Ficoll method; adherent cells are separated from non-adherent cells; the adherent cells are then cultured in the presence of GM-CSF and IL-4 to induce dendritic cells; and the dendritic cells are pulsed by culturing with a peptide of the invention to obtain the APCs of the invention. The dendritic cells should be exposed to the peptide for sufficient time to allow the antigen to be internalized and presented on the dendritic cells surface. The resulting dendritic cells can then be re-administrated to the patient to be treated. Such methods are described in WO93/208185 and EP0563485, which are incorporated by reference.

Lymphocytes T and Uses Thereof

Another aspect of the invention is a T lymphocyte that recognizes specifically the peptide of 15 or 16 amino acids long that comprises or consists of the amino acid sequence: REEYARFDSDVGEYR (SEQ ID NO: 1) or a function-conservative variant thereof of the invention.

In one embodiment, said peptide is selected from the group consisting of:

REEYARFDSDVGEYR; (SEQ ID NO: 1)

NREEYARFDSDVGEYR; (SEQ ID NO: 2)

REEYARFDSDVGEFR; (SEQ ID NO: 3)

REEYVRFDSDVGEYR; (SEQ ID NO: 4)

QEEYARFDSDVGEYR; (SEQ ID NO: 5)

REEYARFDSDVGVYR; (SEQ ID NO: 6)

NREEYARFDSDVGEFR; (SEQ ID NO: 7)

NREEYVRFDSDVGEYR; (SEQ ID NO: 8)

NQEEYARFDSDVGEYR (SEQ ID NO: 9)

or

NREEYARFDSDVGVYR. (SEQ ID NO: 10)

In one embodiment of the invention, said T lymphocyte is a regulatory T lymphocyte (Treg). In another embodiment of the invention, said T lymphocyte is a T reg clone.

As used herein, the terms "regulatory T cell" or "regulatory T lymphocyte" are used interchangeably and refer to a specific population of T lymphocytes that have the capacity to dominantly suppress the proliferation of responder T cells in vitro and inhibit diseases and conditions associated with or caused by an excessive immune response such as for example autoimmune diseases, transplantation rejection or a graft versus host disease. Treg were originally identified as a $CD4^+CD25^+$ cell population, but are also characterized by the expression of the forkhead family transcription factor, FoxP3. More recently, $CD8^+$ Treg cells have also been identified as previously described.

In a particular embodiment, said Treg is a $CD8^+$ $CD45RC^{low}$ Treg.

In another embodiment, said T lymphocyte is a genetically modified T lymphocyte that expresses a TCR that recognizes specifically the peptide of the invention.

Accordingly, the T lymphocyte expresses a biased restricted TCR repertoire. Biased (TCR) is well known form the skilled man in the art. Examples of TCR bias have been observed in classical polymorphic major histocompatibility complex (MHC)-restricted immune responses and have been described (64).

Methods for Obtaining a Population of Regulatory T Cells

In another aspect, the invention relates to an in vitro or ex vivo method for generating a population of Tregs, comprising a step of culturing a population of Tregs with a culture medium comprising an isolated peptide of length ranging between 15 and 40 amino acids which is derived from a MHC class II molecule that comprises the amino acid sequence: REEYARFDSDVGEYR (SEQ ID NO: 1) or a function-conservative variant thereof according the invention in the presence of a population of dendritic cells.

In one embodiment, said peptide consists of the amino acid sequence: RLLARLIYNREEYARFDSDVGEYRAV-TELGRPSAEYRNKQ (SEQ ID NO: 28) or a function-conservative variant thereof.

In one embodiment, the invention relates to an in vitro or ex vivo method for generating a population of $CD8^+$ $CD45RC^{low}$ Tregs, comprising a step of culturing a population of $CD8^+$ Tregs with a culture medium comprising an isolated peptide of the invention in the presence of a population of plasmacytoid dendritic cells (pDCs).

In one embodiment, pDCs are mature pDCs.

In one embodiment, said isolated peptide is an isolated peptide of 15 or 16 amino acids long that comprises or consists of the amino acid sequence: REEYARFDSD-VGEYR (SEQ ID NO: 1) (also called herein 51-18) or a function-conservative variant thereof In a particular embodiment, said isolated peptide selected from the group consisting of:

REEYARFDSDVGEYR;    (SEQ ID NO: 1)

NREEYARFDSDVGEYR;   (SEQ ID NO: 2)

REEYARFDSDVGEFR;    (SEQ ID NO: 3)

REEYVRFDSDVGEYR;    (SEQ ID NO: 4)

QEEYARFDSDVGEYR;    (SEQ ID NO: 5)

REEYARFDSDVGVYR;    (SEQ ID NO: 6)

NREEYARFDSDVGEFR;   (SEQ ID NO: 7)

NREEYVRFDSDVGEYR;   (SEQ ID NO: 8)

NQEEYARFDSDVGEYR    (SEQ ID NO: 9)
or

NREEYARFDSDVGVYR.   (SEQ ID NO: 10)

As used herein, the term "culture medium" refers to any medium capable of supporting the growth and the differentiation of T cells into regulatory T cells. Typically, it consists of a base medium containing nutrients (a source of carbon, aminoacids), a pH buffer and salts, which can be supplemented with growth factors and/or antibiotics. Typically, the base medium can be RPMI 1640, DMEM, IMDM, X-VIVO or AIM-V medium, all of which are commercially available standard media.

Preferred media formulations that will support the growth and the differentiation of naive T cells into regulatory T cells include chemically defined medium (CDM). As used herein, the term "chemically defined medium" (CDM) refers to a nutritive solution for culturing cells which contains only specified components, preferably components of known chemical structure. A chemically defined medium is a serum-free and feeder-free medium.

The step of culturing a population of CD8$^+$ Tregs with the peptide of the invention in the presence of a population of pDCs shall be carried out for the necessary time required for the presentation of said peptide by the pDCs to the CD8$^+$ Tregs.

Typically, the culture of a population of CD8$^+$ Tregs with the peptide of the invention in the presence of a population of pDCs shall be carried from 1 day to 1 week or more.

In a particular embodiment, the method may comprise an additional step of isolating the population of regulatory T cells thus generated.

Alternatively, the invention relates to an in vitro or ex vivo method for generating a population of Tregs, comprising a step of culturing a population of Tregs with a culture medium comprising a MHC/peptide multimer of the invention as defined above.

In one embodiment, the invention relates to an in vitro or ex vivo method for generating a population of CD8$^+$ CD45RC$^{low}$ Tregs, comprising a step of culturing a population of CD8$^+$ Tregs with a culture medium comprising a MHC/peptide multimer of the invention as defined above.

In one embodiment, the multimer is coated on a nanoparticle. Thus, the nanoparticle displays at its surface the MHC/peptide multimer according to the invention.

Within the context of the invention, the nanoparticles are of small size, small enough to be recognized by Tregs. In preferred embodiments, the nanoparticles have a core with a mean diameter between 0.5 and 10 nm, more preferably between 1 and 2.5 nm.

The core of the nanoparticle may be a polymeric core. Preferably, the nanoparticle comprises polymers are selected from the group consisting of carbohydrate-based polymers (e.g., cellulose-based nanoparticles, chitosan-based nanoparticles), polyethylene glycol (PEG), polypropylene glycol (PPG), and copolymers of PEG and PPG, branched copolymers containing PEG and caprolactone, PEG and lactide, and PEG and [lactide-co-glycolide].

The core of the nanoparticle may also be a metallic core. Preferably, the metallic core comprises Au, Ag or Cu, for example an alloy selected from Au/Ag, Au/Cu, Au/Ag/Cu, Au/Pt, Au/Pd, Au/Ag/Cu/Pd, Au/Fe, Au/Cu, Au/Gd, Au/Fe/Cu, Au/Fe/Gd or Au/Fe/Cu/Gd.

Preferably, the nanoparticles are soluble in most organic solvents and especially water. Nanoparticles can be prepared according to techniques well-known in the art.

In one embodiment, the invention relates to an in vitro or ex vivo method for generating a population of CD8$^+$ CD45RC$^{low}$ Tregs, comprising a step of culturing a population of CD8$^+$ Tregs with a culture medium comprising nanoparticles coated with a MHC/peptide multimer of the invention as defined above.

In another aspect, the invention relates to a population of Tregs, more particularly a population of CD8$^+$CD45RC$^{low}$ Tregs, obtained by any one of the methods as previously described.

Pharmaceutical Compositions

Another aspect of the invention relates to a pharmaceutical composition comprising:
a) an isolated peptide of length ranging between 15 and 40 amino acids which is derived from a MHC class II molecule that comprises the amino acid sequence: REEYARFDSDVGEYR (SEQ ID NO: 1) or a function-conservative variant thereof; or
b) an acid nucleic encoding a peptide of the invention; or
c) a vector comprising such nucleic acid; or
d) a host cell comprising such expression vector; or
e) a complex MHC molecule and a peptide of the invention; or
f) an antigen-presenting cell comprising a complex MHC molecule and a peptide of the invention; or
g) a T lymphocyte that recognizes specifically the peptide of the invention;
and a pharmaceutically acceptable carrier.

In a particular embodiment, said peptide consists of the amino acid sequence: RLLARLIYNREEYARFDSDVGEY-RAVTELGRPSAEYRNKQ (SEQ ID NO: 28) or a function-conservative variant thereof.

In one embodiment, said pharmaceutical composition comprises an isolated peptide of 15 or 16 amino acids long that comprises or consists of the amino acid sequence: REEYARFDSDVGEYR (SEQ ID NO: 1) or a function-conservative variant thereof In a particular embodiment, said pharmaceutical composition comprises an isolated peptide selected from the group consisting of:

REEYARFDSDVGEYR; (SEQ ID NO: 1)

NREEYARFDSDVGEYR; (SEQ ID NO: 2)

REEYARFDSDVGEFR; (SEQ ID NO: 3)

REEYVRFDSDVGEYR; (SEQ ID NO: 4)

QEEYARFDSDVGEYR; (SEQ ID NO: 5)

REEYARFDSDVGVYR; (SEQ ID NO: 6)

NREEYARFDSDVGEFR; (SEQ ID NO: 7)

NREEYVRFDSDVGEYR; (SEQ ID NO: 8)

NQEEYARFDSDVGEYR (SEQ ID NO: 9)
or

NREEYARFDSDVGVYR. (SEQ ID NO: 10)

Any therapeutic agent of the invention as above described may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

To prepare pharmaceutical compositions, an effective amount of a polypeptide or a nucleic acid according to the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

The peptides according to the invention and other therapeutic agent of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g. tablets or other solids for oral administration; time release capsules; and any other form currently used.

Therapeutic Methods and Uses

The invention provides methods and compositions (such as pharmaceutical compositions) for use in inducing immune tolerance in a patient in need thereof.

The invention also provides methods and compositions for use in preventing or reducing transplant rejection in a patient in need thereof.

Accordingly, the invention relates to an isolated peptide of length ranging between 15 and 40 amino acids which is derived from a MHC class II molecule that comprises the amino acid sequence: REEYARFDSDVGEYR (SEQ ID NO: 1) (also called herein 51-18) or a function-conservative variant thereof as defined above for use as drug.

In one embodiment, said peptide consists of the amino acid sequence: RLLARLIYNREEYARFDSDVGEYRAVTELGRPSAEYRNKQ (SEQ ID NO: 28) or a function-conservative variant thereof.

In one embodiment, said peptide is an isolated peptide of 15 or 16 amino acids long that comprises or consists of the amino acid sequence: REEYARFDSDVGEYR (SEQ ID NO: 1) or a function-conservative variant.

In another aspect, the invention relates to an isolated peptide of length ranging between 15 and 40 amino acids which is derived from a MHC class II molecule that comprises the amino acid sequence: REEYARFDSDVGEYR (SEQ ID NO: 1) (also called herein 51-18) or a function-conservative variant thereof as defined above for use in inducing immune tolerance in a patient in need thereof.

In one embodiment, said peptide consists of the amino acid sequence: RLLARLIYNREEYARFDSDVGEYRAVTELGRPSAEYRNKQ (SEQ ID NO: 28) or a function-conservative variant thereof.

In one embodiment, said peptide is an isolated peptide of 15 or 16 amino acids long that comprises or consists of the amino acid sequence: REEYARFDSDVGEYR (SEQ ID NO: 1) or a function-conservative variant for use in inducing immune tolerance in a patient in need thereof.

As used herein, the term "immune tolerance" refers to a state of unresponsiveness of the immune system to substances or tissues that have the capacity to elicit an immune response. Peptides of the invention are useful for achieving tolerance or partial tolerance against the transplant upon transplantation of said transplant. As used herein, a "partial tolerance" is a partial immune tolerance results in a reduced immune response.

As used herein, the term "immune response" includes T cell mediated and/or B cell mediated immune responses. Exemplary immune responses include T cell responses, e.g., cytokine production and cellular cytotoxicity, in addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells ($CD4^+$, $CD8^+$, Th1 and Th2 cells); antigen presenting cells (e.g. professional antigen presenting cells such as dendritic cells); natural killer cells; myeloid cells, such as macrophages, eosinophils, mast cells, basophils, and granulocytes.

For instance, immune responses are involved in transplant rejection, as well as in the concomitant physiological result of such immune responses, such as for example, interstitial fibrosis, chronic graft arteriosclerosis, or vasculitis.

Thus, treated patients with a peptide of the invention (as well as with a MCH/peptide mutimer of the invention, or peptide-specific Tregs as defined herein) in comparison with untreated patients, display the following physiological features: a) a decreased level of an immune response against the transplant (thought to be mediated at least in part by B cell mediated immune responses, more particularly donor-specific antibodies); b) a delay in the onset or progression of a immune response against the transplant; or c) a reduced risk of the onset or progression of an immune response against the transplant.

By "patient in need thereof" is meant an individual suffering from or susceptible of suffering from transplant rejection to be treated. The individuals to be treated in the frame of the invention are mammals, preferably human beings.

In still another aspect, the invention relates to an isolated peptide of length ranging between 15 and 40 amino acids which is derived from a MHC class II molecule that comprises the amino acid sequence: REEYARFDSDVGEYR (SEQ ID NO: 1) (also called herein 51-18) or a function-conservative variant thereof as defined above for use in preventing or reducing transplant rejection in a patient in need thereof.

In one embodiment, said peptide consists of the amino acid sequence: RLLARLIYNREEYARFDSDVGEYRAV-TELGRPSAEYRNKQ (SEQ ID NO: 28) or a function-conservative variant thereof.

In one embodiment, said peptide is an isolated peptide of 15 or 16 amino acids long that comprises or consists of the amino acid sequence: REEYARFDSDVGEYR (SEQ ID NO: 1) or a function-conservative variant.

As used herein, the term "preventing or reducing transplant rejection" is meant to encompass prevention or inhibition of immune transplant rejection, as well as delaying the onset or the progression of immune transplant rejection. The term is also meant to encompass prolonging survival of a transplant in a patient, or reversing failure of a transplant in a patient. Further, the term is meant to encompass ameliorating a symptom of an immune transplant rejection, including, for example, ameliorating an immunological complication associated with immune rejection, such as for example, interstitial fibrosis, chronic graft arteriosclerosis, or vasculitis.

As used herein, the term "transplant rejection" encompasses both acute and chronic transplant rejection. "Acute rejection" is the rejection by the immune system of a tissue transplant recipient when the transplanted tissue is immunologically foreign. Acute rejection is characterized by infiltration of the transplant tissue by immune cells of the recipient, which carry out their effector function and destroy the transplant tissue. The onset of acute rejection is rapid and generally occurs in humans within a few weeks after transplant surgery. Generally, acute rejection can be inhibited or suppressed with immunosuppressive drugs such as rapamycin, cyclosporin and the like. "Chronic rejection" generally occurs in humans within several months to years after engraftment, even in the presence of successful immunosuppression of acute rejection. Fibrosis is a common factor in chronic rejection of all types of organ transplants.

The term "transplantation" and variations thereof refers to the insertion of a transplant (also called graft) into a recipient, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, including animals from phylogenically widely separated species, for example, a baboon heart being transplanted into a human host.

In one embodiment the donor of the transplant is a human. The donor of the transplant can be a living donor or a deceased donor, namely a cadaveric donor.

In one embodiment, the transplant is an organ, a tissue or cells.

As used herein, the term "organ" refers to a solid vascularized organ that performs a specific function or group of functions within an organism. The term organ includes, but is not limited to, heart, lung, kidney, liver, pancreas, skin, uterus, bone, cartilage, small or large bowel, bladder, brain, breast, blood vessels, esophagus, fallopian tube, gallbladder, ovaries, pancreas, prostate, placenta, spinal cord, limb including upper and lower, spleen, stomach, testes, thymus, thyroid, trachea, ureter, urethra, uterus. As used herein, the term "tissue" refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

In a particular embodiment of the invention, the transplant is a cardiac allotransplant.

As used herein, the term "cells" refers to a composition enriched for cells of interest, preferably a composition comprising at least 30%, preferably at least 50%, even more preferably at least 65% of said cells.

In certain embodiments the cells are selected from the group consisting of multipotent hematopoietic stem cells derived from bone marrow, peripheral blood, or umbilical cord blood; or pluripotent (i.e. embryonic stem cells (ES) or induced pluripotent stem cells (iPS)) or multipotent stem cell-derived differentiated cells of different cell lineages such as cardiomyocytes, beta-pancreatic cells, hepatocytes, neurons, etc. . . . .

In one embodiment, the cell composition is used for allogeneic hematopoietic stem cell transplantation (HSCT) and thus comprises multipotent hematopoietic stem cells, usually derived from bone marrow, peripheral blood, or umbilical cord blood.

HSCT can be curative for patients with leukemia and lymphomas. However, an important limitation of allogeneic HCT is the development of graft versus host disease (GVHD), which occurs in a severe form in about 30-50% of humans who receive this therapy.

Peptides of the invention are useful in inducing immune tolerance and thus in preventing or reducing Graft-versus-Host-Disease (GvHD).

Accordingly, in one embodiment, the patient in need thereof is affected with a disease selected from the group consisting of acute myeloid leukemia (AML); acute lymphoid leukemia (ALL); chronic myeloid leukemia (CML); myelodysplasia syndrome (MDS)/myeloproliferative syndrome; lymphomas such as Hodgkin and non-Hodgkin lymphomas, chronic lymphatic leukemia (CLL) and multiple myeloma.

In another aspect, the invention relates to
a) an acid nucleic encoding a peptide of the invention; or
b) a vector comprising such nucleic acid; or
c) a host cell comprising such expression vector; or
d) a MHC/peptide multimer of the invention; or
e) an antigen-presenting cell comprising a complex MHC molecule and a peptide of the invention; or
f) a T lymphocyte that recognizes specifically the peptide of the invention; for use in inducing immune tolerance in a patient in need thereof.

In still another aspect, the invention relates to
a) an acid nucleic encoding a peptide of the invention; or
b) a vector comprising such nucleic acid; or
c) a host cell comprising such expression vector; or
d) a MHC/peptide multimer of the invention; or
e) an antigen-presenting cell comprising a complex MHC molecule and a peptide of the invention; or
f) a T lymphocyte that recognizes specifically the peptide of the invention; for use in preventing or reducing transplant rejection in a patient in need thereof.

Another aspect of the invention relates to a method for inducing immune tolerance in a patient in need thereof, comprising a step of administering to said patient a prophylactically effective amount of an isolated peptide of the invention as described above, or a nucleic acid of the invention, or an expression vector of the invention, or a host cell of the invention, or a MHC/peptide multimer of the invention, or a T lymphocyte that recognizes specifically the peptide of the invention.

Another aspect of the invention relates to a method for preventing or reducing transplant rejection in a patient in need thereof, comprising a step of administering to said patient a prophylactically effective amount of an isolated peptide of the invention as described above, or a nucleic acid of the invention, or an expression vector of the invention, or a host cell of the invention, a MHC/peptide multimer of the invention or a T lymphocyte that recognizes specifically the peptide of the invention.

As used herein, the term "prophylactically effective amount" is intended for a minimal amount of active agent, which is necessary to prevent, reduce, alleviate or delay) transplant rejection in a patient.

Diagnostic Methods of the Invention

In a still further aspect, the invention relates to an in vitro method for determining whether a transplanted patient (recipient) is tolerant, comprising a step of determining the presence of CD8+CD45RC$^{low}$ Tregs in a biological sample obtained from said transplanted patient, wherein the presence of CD8+CD45RC$^{low}$ Tregs is indicative of tolerance.

As used herein, the term "determining" includes qualitative and/or quantitative detection (i.e. detecting and/or measuring the amount) with or without reference to a control or a predetermined value. As used herein, "detecting" means determining if CD8+CD45RC$^{low}$ Tregs are present or not in a biological sample and "measuring" means determining the amount of CD8+CD45RC$^{low}$ Tregs in a biological sample.

As used herein, the term "biological sample" has its general meaning in the art and refers to any sample which may be obtained from a patient for the purpose of in vitro evaluation. A preferred biological sample is a blood sample (e.g. whole blood sample, serum sample, or plasma sample).

For example, the determination of the presence of CD8+CD45RC$^{low}$ Tregs may comprise a step of contacting the biological sample with selective reagents such as antibodies, and thereby detecting the presence, or measuring the amount, of cells of interest originally in said biological sample. Contacting may be performed in any suitable device, such as a plate, microtiter dish, test tube, well, glass, column, and so forth.

Accordingly, the methods according to the invention comprise a step of contacting the biological sample with a binding partner capable of selectively interacting with CD8+CD45RC$^{low}$ Tregs in said biological sample.

In one embodiment of the invention, the binding partner is a MHC/peptide multimer comprising a peptide of the invention as described here above.

In a preferred embodiment, the MHC/peptide multimer is a MHC/peptide tetramer comprising a peptide selected from the group consisting of:

REEYARFDSDVGEYR; (SEQ ID NO: 1)

NREEYARFDSDVGEYR; (SEQ ID NO: 2)

REEYARFDSDVGEFR; (SEQ ID NO: 3)

REEYVRFDSDVGEYR; (SEQ ID NO: 4)

QEEYARFDSDVGEYR; (SEQ ID NO: 5)

REEYARFDSDVGVYR; (SEQ ID NO: 6)

NREEYARFDSDVGEFR, (SEQ ID NO: 7)

NREEYVRFDSDVGEYR, (SEQ ID NO: 8)

NQEEYARFDSDVGEYR (SEQ ID NO: 9)

or

NREEYARFDSDVGVYR. (SEQ ID NO: 10)

In one embodiment, the patient is a mammal, preferably a human being.

The invention will be further illustrated by the following figures and examples. However, these examples and figures should not be interpreted in any way as limiting the scope of the present invention.

FIGURES

FIG. 1: Analysis of CD8$^+$CD45RC$^{low}$ Tregs activation in response to donor-derived peptide stimulation. (A) CD8$^+$ Tregs were cocultured for 6 days with syngeneic CpG-matured pDCs in the presence of peptides. For each experiment, the percentage of CD25 positive Tregs after 6 days of coculture with pDCs only, was given the value 1. Mean value 1 is equal to 32.85±1.98%. Results are expressed as the ratio±SEM between the percentage of CD25 positive cells after peptide stimulation and percentage of CD25 positive cells in the control condition without peptide. *p<0.05, p<0.01 and *p<0.001 versus control condition (value 1.0). n=4 to 18 for each peptide. (B) Analysis of Treg activation in response to Du51 shorter peptide derivatives. On the left, 18 Du51-derivatives are detailed and classified by aa sequence length, from 9 aa to 15 aa. The box highlights mismatched aa between the donor and recipient. On the right, Treg activation in response to Du51-derivatives was analyzed by CD25 expression. CD8$^+$ Tregs were cocultured for 6 days with syngeneic CpG-matured pDCs in the presence of each peptide. Bars represent the ratio between the percentage of CD25 positive cells after peptide stimulation and percentage of CD25 positive cells in the control condition without peptide. *p<0.05, p<0.01 and *p<0.001 versus Du51 condition. n=3 to 14 for each peptide.

Figure 2:
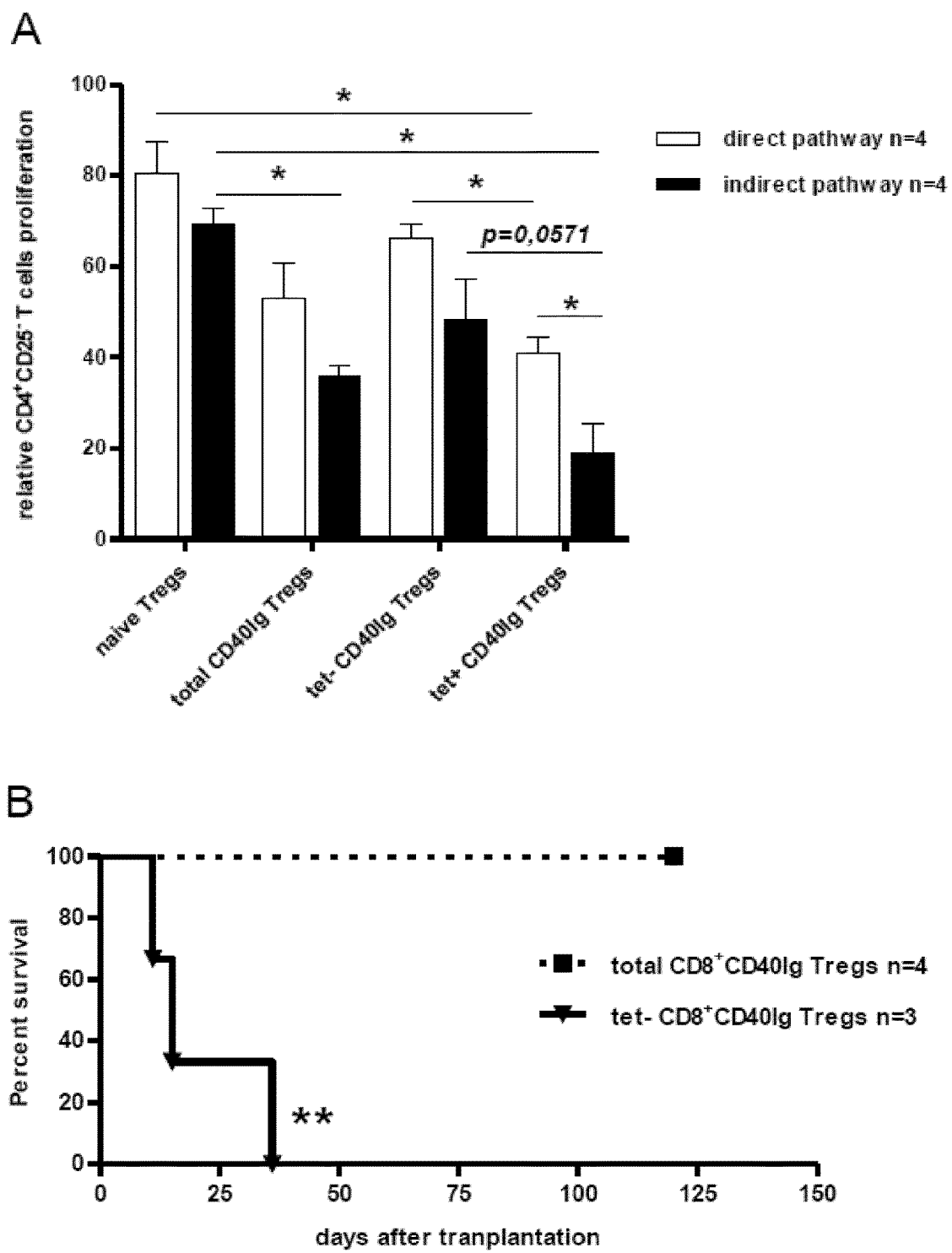

FIG. 2: In vitro and in vivo suppressive potential of Du51-specific CD40IgCD8$^+$ Tregs. (A) The proliferation of naive CFSE-labeled LEW.1A CD4$^+$CD25$^-$ T cells stimulated with either donor LEW.1W (direct pathway) or alloantigens-loaded recipient LEW.1A (indirect pathway) pDCs was analyzed after 6 days of culture, in the absence or presence of LEW.1A naive, total, tetramer$^-$ or tetramer$^+$ CD8$^+$CD40Ig Tregs at a 1:1 effector:suppressor ratio. The CD4$^+$CD25$^-$ T cell proliferation alone was 80% and was given the value 100 in each experiment. Graphs represent the mean±SEM of relative CD4$^+$CD25$^-$ T cell proliferation. *p<0.05. n=4. (B) 2.5×10$^6$ total or tetramer$^-$ CD8$^+$CD40Ig Tregs were injected i.v into sublethally irradiated recipients (LEW.1A) the day before heart allotransplantation (LEW.1W). Graft survival was assessed by abdominal palpation of cardiac beating. p<0.01 for total (n=4) versus tetramer− CD8+CD40Ig Tregs (n=3).

FIG. 3: Tolerance induction after in vivo peptide Du51 infusion. (A) Recipients were either untreated (n=9), treated with 5 single i.v injections of 0.5 mg peptide at day −6, −3 pre-graft, day 0, +3 and +7 post-graft (n=4), or treated with continuous infusion of peptide by i.p mini osmotic pumps (ALZET), delivering from day-7 and for 28 days, either 20.83 µg/hour alone (Du51 0.5 mg/day: n=8) or combined with a depleting anti-CD8 mAb (OX8) (n=6) or an anti-MHC class I mAb (OX18) (n=5), or 40.66 µg/hour in the LEW.1W/LEW.1A (Du51 1 mg/day: n=5) or BN/LEW.1A (Du51 1 mg/day (BN/1A): n=4) strains combination. **p<0.01 Du51 0.5 mg/day versus untreated animals and control peptide 0.5 mg/day. *p<0.05 Du51 0.5 mg/day+ depleting anti-CD8 mAb versus Du51 0.5 mg/day. *p<0.001 Du51 1 mg/day versus untreated animals. p<0.01 Du51 1 mg/day versus Du51 1 mg/day in BN/1A combination. *p<0.05 Du51 1 mg/day versus Du51 0.5 mg/day. (B) Alloantibody production was evaluated in naive (n=3), grafted syngeneic (n=3), grafted untreated (n=3), CD40Ig-treated (n=3), long-term Du51-treated (n=2) and rejected Du51-treated (n=4) animals. Sera were collected <30 days after rejection or >120 days after transplantation. Sera were incubated with donor splenocytes and analyzed by flow cytometry for IgG, IgG1, IgG2a or IgG2b Abs production. Graph represents MFI±SEM. *p<0.05, p<0.01, *p<0.001, ****p<0.0001. (C) Spleens were recovered after rejection or at day 120 and cell populations were stained and analyzed by flow cytometry. Graph represents the absolute number of each sub-population in the total spleen from either (n=12), long-term Du51-treated (n=2) or rejected Du51-treated recipients (n=5). (D) Spleen of naive (n=4), long-term Du51-treated (n=2) or rejected Du51-treated (n=4) recipients were incubated with RT1.A$^a$/Du51 tetramers labeled with streptavidin conjugated to PE and APC. Results are plotted into graphs for percentage of tetramer+ cells among CD8+ Tregs and absolute number of tetramer+ CD8+ Tregs in spleen ±SEM.

Figure 4:
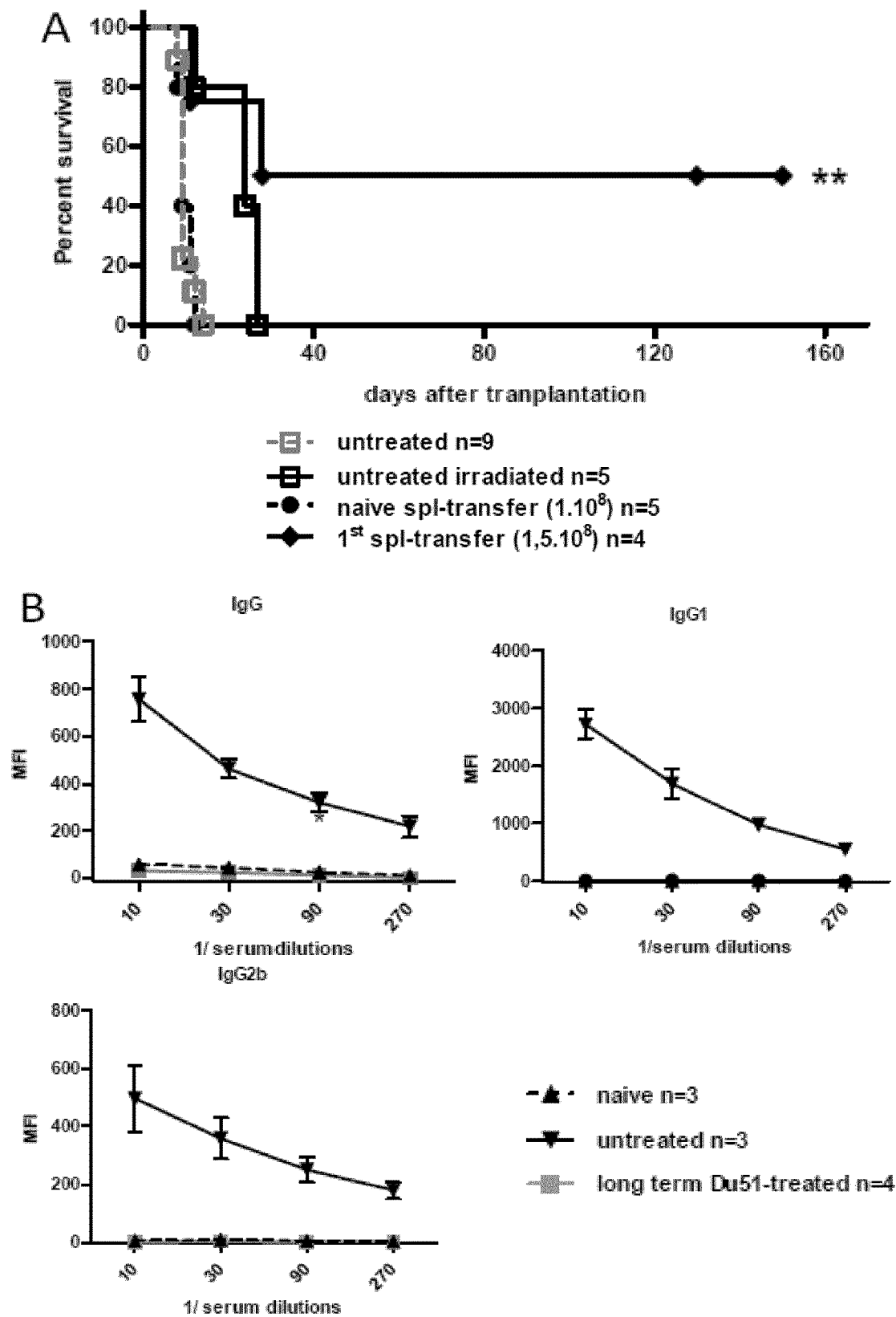

FIG. 4: Splenocyte-mediated transfer of tolerance following Du51 peptide monotherapy. A. LEW.1A recipients were sublethally irradiated (4.5 Gy) at day 1 and received heart allografts and i.v. injections of $1.5 \cdot 10^8$ splenocytes from long surviving recipient or naive animals at day 0. Graft survival was monitored by abdominal palpation. B. IgG alloantibody production was evaluated in naive (n 3), untreated recipients that had rejected their graft (n=3) and 1$^{st}$ spl-transferred long-term recipients more than 120 days after transplantation.

EXAMPLE

MHCII+ Allopeptide Induce Tolerance

Material & Methods

Animals and Cardiac Transplantation Models:

Allotransplantations of heart were performed between whole MHC incompatible LEW.1W (RT1.A$^u$ as donors) and LEW.1A (RT1.A$^a$ as recipients) male rats as previously described (5). The experiments were approved by the regional ethical committee for animal experimentation.

Adenovirus-Mediated Gene Transfer:

The Ad encoding for the extracellular portion of mouse CD40 fused to the constant domains of human IgG1 (AdCD40Ig) and the recombinant non-coding adenovirus (Ad) Addl324, as well as the procedure of intragraft delivery, have been described previously (5). Briefly, adenoviral particles ($2 \cdot 10^{10}$ infectious particles) were slowly injected at 3 points into the cardiac ventricular walls.

Peptides Libraries:

16-mer overlapping peptide libraries with 4 aa lagging were designed to cover the entire polymorphic sequences of MHC-I RT1.Au (alpha 1, 2 and 3 domains), MHC-II RT1.B$^u$ (all domains) and MHC-II RT1.D$^u$ (alpha2 and beta1 domains) as previously published (17-19) and manufactured by GL Biochem Ltd (Shangai, China). Lyophilized peptides were dissolved in 0.4% sterile DMSO/sterile water and stored at −80° C. As control peptides, we used in vitro various allogeneic non activating peptides #7, 26 and 39 and in vivo, we used peptide #31.

Degenerated 9 to 15-mer overlapping peptides with 1 to 2 aa lagging were designed to cover the sequence of positively isolated 16-mer peptide and synthesized by GL Biochem Ltd (Shangai, China).

All peptides were shown to be >95% homogeneous by analytical reverse phase HPLC and aa sequences were confirmed. Peptides were diluted in complete RMPI-1640 at a concentration of 120 µg/ml.

Cell Purification:

T cells were purified as previously described (6). Briefly, total splenocytes were depleted with a cocktail of anti-γδ T cells (V65), anti-CD45RA cells (OX33), anti-CD161 NK cells (3.2.3) and anti-CD11b/c monocytes (OX42) using magnetic beads (Dynal). Enriched T cells were labeled with anti-CD45RC-biotin (OX22) and Strepavidin-PE-Cy7, anti-CD8α-PE (OX8), anti-TCRαβ-Alexa 647 (R73) and anti-CD25-FITC (OX39) mAbs. CD8+CD45RC$^{low}$ T cells and CD4+CD25− T cells were sorted after gating of TCRαβ+ cells with FACSAria (BD Biosciences, Mountain View, Calif.). Purity of sorted populations was greater than 99%.

Plasmacytoid dendritic cells (pDCs) were purified as previously described (6). Briefly, splenocytes recovered after collagenase digestion were further purified by negative depletion with anti-TCR (R73 and V65) T cells and anti-CD45RA (OX33) B cells mAbs. Enriched cells were labeled with anti-CD45R-PE (His24), anti-CD4-APC (OX35), anti-TCR-FITC (R73) and anti-CD45RA-FITC (OX33). pDCs, defined as CD45R and CD4 positive cells, were sorted after gating on FITC negative cells.

Mixed Lymphocyte Reaction:

For MLR coculture assays, pDCs from LEW.1A naive rats ($1.25 \times 10^4$ cells), syngeneic CD8+CD40Ig Tregs ($5 \times 10^4$ cells) and 120 µg/ml of allogeneic peptides were plated in triplicate in 200 µl of complete RPMI-1640 medium in round-bottom 96 wells plates for 6 days at 37° C., 5% CO2. pDCs were matured with 0.5 µM of CpG ODN 1826.

For direct MLR suppressive assays, sorted CFSE-labeled CD4+CD25− T cells from LEW.1A origin ($5 \times 10^4$ cells) and allogeneic pDCs isolated from donor LEW.1W animals ($1.25 \times 10^4$ cells) were plated in triplicate for 6 days in a final volume of 200 µl of completed RPMI-1640 medium in round-bottom 96 wells plates with FACS-sorted freshly purified naive CD8+CD45RC$^{low}$ Treg cells, peptide-expanded CD8+CD40Ig Treg cells ($5 \times 10^4$ cells), Du51 tetramer+ or − CD8+CD40Ig Tregs. For indirect MLR suppressive assay, splenocytes isolated from donor LEW.1W animals were frozen-thawed to induce apoptosis. Apoptotic cells were then cultured overnight with pDCs isolated from recipient LEW.1A animals (8:1 ratio) at $0.65 \times 10^6$ pDCs/mL. Alloantigens-loaded pDCs were finally washed and plated as described before for the direct MLR.

For anti-CD3/anti-CD28 stimulations, round-bottom 96 wells plates were coated with anti-CD3 (1 µg/mL, BD Pharmingen) and anti-CD28 (10 µg/mL) mAbs for 1 hour at 37° C., 5% CO2, then washed and $5 \cdot 10^4$ CD8$^+$CD40Ig Treg cells were added to each well in 200 µl completed RPMI-1640 for 1, 2, 3 and 6 days.

Proliferation of CFSE-labeled naive CD4$^+$CD25$^-$ T cells and phenotype of CD8$^+$CD45RC$^{low}$ Tregs were analyzed by flow cytometry on a FACSCanto II cytometer (BD Biosciences, Mountain View, Calif.) after gating on TCR$^+$CD4$^+$ cells or TCR$^+$CD8$^+$ cells among live cells (DAPI negative).

Extracellular and Intracellular Staining:

For extracellular staining, cells were stained with the following mAbs: anti-TCRαβ (R73, Alexa Fluor 647-conjugated), anti-CD8α (OX8, PE-Cy7-conjugated, ebiosciences), anti-CD4 (W3.25, PE-Cy7-conjugated), anti-CD45RC (OX22, FITC-conjugated), anti-CD28 (JJ319, biotin-labeled), anti-CD71 (OX26, biotin-labeled), anti-mouse Vb11 (KT11, biotin-labeled, AbD Serotec) anti-CD25 (OX39, biotin-labeled) and anti-MHC-II (OX6, biotin-labeled).

For intracellular staining, cells were then stained for Foxp3 (biotin-labeled, ebiosciences) using BD cytofix/cytoperm kit (BD Biosciences) according to the manufacturer's instructions.

All biotinylated mAbs were visualized using Streptavidin-PerCP.Cy5.5 (BD Biosciences). A FACSCanto II cytofluorimeter (BD Biosciences, Mountain View, Calif.) was used to measure fluorescence, and data were analyzed using FlowJo software (Tree Star, Inc. USA, version 7.6.5). Cells were first gated by their morphology and dead cells excluded by selecting DAPI negative viable cells.

Cytokine Assays:

IFNγ, IL-10 were measured in coculture supernatants using ELISA from BD Biosciences OptEIA, IL-12 and TGFβ using ELISA from Invitrogen and R&D System respectively.

Production of Biotinylated RT1-A$^a$-Peptide Complexes:

Briefly, the heavy chain RT1-A$^a$ and the β2microglobuline (β2m) were cloned in pET24 and produced in *Escherichia coli* BL21-DE3. Recombinant proteins were produced as inclusion bodies, dissolved in 8M urea and refolded in vitro as previously described for human HLA-A2/peptide complexes (61). RT1-A$^a$, β2m and peptide Du51 were refolded in 0.4M L-arginine, 0.1M Tris pH8, 2 mM EDTA, 5 mM reduced glutathione, and 0.5 mM oxydated glutathione for 5 days at 4° C. The solution was then concentrated and the buffer changed on amicon membrane 10 Kd (Millipore, Bedford, Mass.). Folded MHC/peptide complexes were biotinylated with the BirA enzyme (Avidity, Denvers Colo.) for 5 h at 30° C. and desalted on Hiprep 26/10 desalting column (GE Healthcare). MHC/peptide complexes were then purified by anion exchange Q-Sepharose chromatography. Biotinylation was tested by tetramerization with streptavidin (Sigma Aldrich) at a molar ratio of 4:1.

Tetramerization and Staining:

Tetramerization of RT1.A$^a$/Du51 was performed at room temperature by addition of streptavidin-PE (Jackson ImmunoResearch) or streptavidin-APC (BD Biosciences) at a 4:1-molar ratio, in four equal aliquots added at 15-min intervals. Likewise, the control tetramer RT1.A$^a$/MTF-E (ILFPSSERLISNR) was conjugated to streptavidin-BV421 (Biolegend) and represented 1.6+/−0.7% of non-specific staining among Du51-specific cells. These three reagents were mixed and added to plated cells at 10 µg/mL for 1 hour at 4° C. Cells were further stained for CD8 and CD45RC and fluorescence was analyzed on a FACSCanto II cytometer (BD Biosciences, Mountain View, Calif.). Cells were first gated by their morphology and dead cells excluded by selecting DAPI negative cells.

Peptides Treatment In Vivo:

16-mer peptides were dissolved in 0.4% DMSO/PBS before injection. For the first protocol, single doses of peptide (500 µg/injection) were injected i.v at different time points before and after transplantation at day −6, −3, 0 +3 and +7 into grafted LEW.1A recipients. In the second protocol, mini osmotic pumps (ALZET, Cupertino, Calif., USA) were implanted intraperitoneally (i.p) in recipients and delivered continuously either 20.83 or 41.66 µg/hour of 16-mer peptides for 14 days. A first pump was implanted on day −7 before transplantation and was replaced by a second one at day +7, allowing delivery of 14 or 28 mg of peptide per animal for 28 consecutive days. A depleting anti-CD8α mAb (OX8, IgG1, 3 mg/kg) or an anti-MHC class Ia and Ib mAb (OX18, 3 mg/kg) were injected i.p. twice a week from day −7 until rejection. Allografts were monitored daily by palpation and allograft rejection was defined as complete cessation of palpable heart beat.

Adoptive Cell Transfer:

Cell transfers were performed by i.v. injection of purified sorted total or Du51 tetramer$^-$ CD8$^+$CD40Ig Tregs into LEW.1A recipients sublethally irradiated (4.5 Gy whole-body irradiation) on the day before transplantation. Total splenocytes ($1.5 \cdot 10^8$ cells) were adoptively transferred i.v. the day before heart transplantation into naive LEW-1A recipients that had received 4.5 Gy of whole-body irradiation the same day. Recipients received splenocytes from Du51-treated rats (defined as 1$^{st}$ spl-transferred) or from naive rats (naive spl-transferred) or no cells (untreated irradiated).

Morphometric Analysis of Cardiac Grafts:

The upper third of the graft was fixed in paraformaldehyde and embedded in paraffin. Five µm coronal sections were stained with hematoxyline-eosine-safron. Tissues were analyzed by a pathologist (K.R.) blinded to the groups and chronic rejection was evaluated as previously described (63).

Donor Specific Alloantibody Detection:

Alloantibodies were analyzed by cytofluorimetry as described elsewhere (28). Briefly, after digestion by collagenase D and red blood cell lysis, allogeneic spleen cells were incubated with diluted (1/8) heat-inactivated serum, and then with FITC-conjugated goat anti-rat IgG antibodies (H+L chain specific) (Jackson Laboratories), a mouse anti-rat IgG1 MAb (MCA 194, Serotec), IgG2a (MCA 278, Serotec) or IgG2b (MCA 195, Serotec). Antibody binding was revealed using FITC-coupled F(ab)'2 goat anti-mouse IgG (Jackson Laboratories). Cells were analyzed using a FACS Canto II cytofluorimeter (BD Biosciences, Mountain View, Calif.) and the results were expressed as mean channel fluorescence for each serum.

Statistical Analysis:

For the peptide activation test, a non-parametric Wilcoxon signed-rank test, comparing column median to a hypothetical value of 1.0, was done. Statistical significance for the TCR Vβ11 expression, phenotype of activated cells, cytokine expression, proliferation assay and tetramer staining was evaluated by a two-tailed Mann Whitney t test. Graft survival was analyzed by Kaplan-Meier log-rank test. The Two-Way ANOVA test and Bonferroni post-tests were used for donor-specific antibody analysis and splenocyte phenotypic characterization. Analyses were made with GraphPad Prism 5.04 software (GraphPad, San Diego, Calif., USA). For the diversity analysis, Kruskal-Wallis and Dunn's multiple comparison post-test were performed using GraphPad Prism 6.0c. A P-value less than 0.05 was considered significant.

Results

CD8+CD40Ig Tregs Activation In Vitro.

In order to identify TCR recognition of allogeneic MHC/peptide complexes by CD8+CD40Ig Tregs and subsequent activation of their function, we had to select a specific marker of activation allowing analysis by flow cytometry following exposure to antigenic stimulation. Therefore, we screened molecules expressed at different time points by CD8+CD40Ig Tregs upon stimulation with polyclonal anti-CD3 and anti-CD28 antibodies. Expression of molecules on freshly isolated CD8+CD40Ig Tregs has been previously assessed by Q RT-PCR (5) and demonstrated that among these molecules, CD25 and IFNγ were markers distinguishing CD8+CD40Ig Tregs from other cell populations. We analyzed by flow cytometry at day 0, 1, 2, 3 and 6 their expression of CD71, CD25 and IFNγ.

We confirmed, at day 0, that CD8+CD40Ig Tregs expressed low levels of CD71 (0.83±0.1%), CD25 (12.74±6.1%), and IFNγ (5.57±3.3%). After polyclonal stimulation, CD71, CD25 and IFNγ expression increased significantly from the first day and remained stable over time with respectively 82±4.5%, 98.1±1.9% and 91.7±7% of positive cells at day 6.

In conclusion, we identified three markers of interest to CD8+CD40Ig Tregs with low basal expression and significant up-regulation upon stimulation. Since CD25 was the most and the earliest up-regulated marker and since it was a marker previously described by us and others (5, 12), we selected this marker to assess CD8+CD40Ig Treg activation for the remaining aspects of this study.

CD8+CD40Ig Tregs Cells Recognized Two Donor MHC Class 11-Derived Peptides.

In the rat MHC-mismatched heart allograft model, donors (RT1$^u$) and recipients (RT1$^a$) are mismatched for all MHC molecules. We therefore aligned donor and recipient MHC I and II amino acids (aa) sequences and designed 82 overlapping 16-mer peptides matching the polymorphic domains of donor MHC I and II molecules (17-19). Peptides were first grouped into pools of 6 to 8 peptides (30 μg/ml of each peptide) and tested in an in vitro assay where immature or mature syngeneic recipient pDCs and sorted-CD8+CD40Ig Tregs from CD40Ig-treated long-term allograft bearing recipients were cocultured for 3 or 6 days. With immature pDCs, we observed no significant activation of CD8+CD40Ig Tregs at day 3 or day 6 with any of the allogeneic pools of peptides. After stimulation with mature pDCs and pools of allogeneic peptides we observed at day 3 a slight upregulation of CD25 expression of a small population of CD8+CD40Ig Tregs, and at day 6, a significant up-regulation of CD25 expression following allogeneic stimulation. These results suggested that some allogeneic peptides were efficiently recognized by CD8+CD40Ig Tregs and that this recognition led to increased CD25 expression. It also demonstrated that pDCs must be matured in our assay.

We next tested the stimulatory capacity of the 82 individual allopeptides in the presence of naive matured syngeneic pDCs and CD8+CD40Ig Tregs purified from long-term survivors in a 6 days culture (FIG. 1A). We observed that two peptides induced a highly significant upregulation of CD25 expression at the cell surface of CD8+CD40Ig Tregs: peptide #31 (called Bu31, 1.67±0.09 fold vs. no peptide, p<0.0001), whose sequence overlaps with peptide #32 sequence (p<0.05), and peptide #51 (called Du51, 2.07±0.18 fold vs. no peptide, p<0.001). Du51 induced a stronger upregulation of CD25 expression compared to Bu31, suggesting that Du51 is the dominant peptide recognized by CD8+CD40Ig Tregs, while Bu31 is sub-dominant. These results demonstrated that antigen-specific CD8+CD40Ig Tregs mainly recognized two peptides, Bu31 (YLRYDSDVGEYRAVTE) and Du51 (NREEYARFDSDVGEYR), derived respectively from the 131 chain of donor MHC class II RT1.B$^u$ and RT1.D$^u$ molecules.

CD8+CD40Ig Tregs Recognized an Unusually Long Allogeneic 15-Mer Peptide.

To determine the sequence of the natural dominant donor peptide recognized by antigen-specific CD8+CD40Ig Tregs, we used a library of degenerated peptides, ranging from 9-mer peptides with one aa lagging to 15-mer peptides with two or more aa lagging derived from the dominant 16-mer Du51 (labeled #51-1 to #51-18) (FIG. 1B and Table 1). This library's design was based on previous results and published reports (20-23) and tested in the same in vitro assay described above. Interestingly, random peptide libraries have established that rat MHC class I RT1-A$^a$ molecules showed a strong preference for 9 to 15 mer peptides bearing an arginine (R) at the C terminus (23).

TABLE 1

List of peptides used in the present study:

| Name | Sequence | Length (aa) | SEQ ID NO: |
|---|---|---|---|
| Du51 | NREEYARFDSDVGEYR | 16 | 2 |
| 51-1 | NREEYARFD | 9 | 11 |
| 51-2 | REEYARFDS | 9 | 12 |
| 51-3 | EEYARFDSD | 9 | 13 |
| 51-4 | EYARFDSDV | 9 | 14 |
| 51-5 | YARFDSDVG | 9 | 15 |
| 51-6 | ARFDSDVGE | 9 | 16 |
| 51-7 | RFDSDVGEY | 9 | 17 |
| 51-8 | FDSDVGEYR | 9 | 18 |
| 51-9 | YARFDSDVGE | 10 | 19 |
| 51-10 | EYARFDSDVG | 10 | 20 |
| 51-11 | EYARFDSDVGE | 11 | 21 |
| 51-12 | YARFDSDVGEY | 11 | 22 |
| 51-13 | YARFDSDVGEYR | 12 | 23 |
| 51-14 | EYARFDSDVGEY | 12 | 24 |
| 51-15 | EEYARFDSDVGE | 12 | 25 |
| 51-16 | EEYARFDSDVGEY | 13 | 26 |
| 51-17 | EEYARFDSDVGEYR | 14 | 27 |
| 51-18 | REEYARFDSDVGEYR | 15 | 1 |

None of the derivative 9-mer peptides #51-1 to #51-8 was able to induce activation of CD8+CD40Ig Tregs equivalent to the one observed with the 16-mer Du51. However, we were able to induce a much stronger and significant CD25 upregulation with a 15-mer derivative peptide (51-18) (2.04±0.3 fold vs. no peptide) missing the N-term asparagine (N). Contrary to other derivatives, CD25 upregulation induced by peptide #51-18 was not significantly different from that induced by Du51 (FIG. 1B).

Altogether, these results showed that a dominant MHC class II-derived 15-mer natural peptide (REEYARFDSD-VGEYR) was presented to the CD8$^+$CD40Ig Tregs and that such presentation induced activation of the specific cells.

Du51-Activated CD8$^+$CD40Ig Treg Cells Displayed a Modified Phenotype and Efficiently Suppressed Antigen-Specific Activated T Cells.

The phenotype of Du51-activated CD8$^+$CD40Ig Tregs was analyzed 6 days after stimulation. We previously demonstrated that CD8$^+$CD40Ig Tregs acted through secretion of high levels of IFNγ, that in turn induced IDO expression by DCs and graft ECs and this action was necessary for tolerance induction in vivo (5). According to these results, we observed that stimulation of CD8$^+$ Tregs by the peptide in the presence of pDCs led to significant increased expression of IFNγ, most likely by activated CD8$^+$CD40Ig Tregs. In the same culture supernatants, we observed decreased IL-12 production, likely of pDC origin, but no modification of IL-10 and TGFβ expression that could be produced by both CD8$^+$CD40Ig Tregs and pDCs. We also observed an upregulation of CD71, CD28 and MHC class II, but no modification of Foxp3 expression after 6 days of peptide stimulation.

We previously demonstrated that CD8$^+$CD40Ig Tregs, in the presence of allogeneic pDCs or syngeneic pDC and a lysate of donor cells, could suppress the proliferation of syngeneic effector CD4$^+$CD25$^-$ T cells, showing that CD8$^+$CD40Ig Tregs acted through the direct and indirect pathway of allorecognition, and that they are more efficient suppressor cells than naive CD8$^+$CD45RC$^{low}$ Tregs (6). Here, we investigated whether Du51-stimulated CD8$^+$CD40Ig Tregs could efficiently suppress effector T cell proliferation after 6 days coculture and thus maintained their suppressor activity, compared to CD8$^+$CD40Ig Tregs stimulated with a non-activating control peptide. We performed a MLR assay stimulating CD8$^+$CD40Ig Tregs for 6 days in the presence of syngeneic pDCs and Du51 or non-activating peptide. Peptides-stimulated CD8$^+$CD40Ig Tregs were then sorted using a FACS Aria and added in a direct MLR assay of sorted allogeneic pDCs and syngeneic CFSE-labeled CD4$^+$CD25$^-$ effector T cells. We hypothesized that expanded-CD8$^+$CD40Ig Tregs would exert bystander regulation of the proliferation of effector CD4$^+$CD25$^-$ T cells stimulated by the direct allorecognition pathway, that was measured 6 days later (24, 25). In the absence of Tregs, 80.5% of CD4$^+$CD25$^-$ effector T cells proliferated. The addition of Du51-stimulated Tregs resulted in a significant inhibition of the proliferation of effector T cells compared to Tregs stimulated by a non-activating peptide. Thus, Du51 antigen-specific CD8$^+$CD40Ig Tregs maintained an efficient suppressive activity after in vitro activation and Tregs that remained unstimulated for 6 days lost their suppressive activity and started to die by neglect.

Identification of Du51-Specific CD8$^+$CD45RC$^{low}$ Tregs Using MHC Class I Tetramer Revealed their Enrichment in CD40Ig-Treated Recipients.

An important challenge in transplantation remains the identification of antigen-specific Tregs as they represent a more potent suppressive population and very few natural epitopes have been identified so far. In addition, to date, in the rat and transplantation settings, no tools were available to directly visualize and detect antigen-specific CD8$^+$ Treg populations. To that end, we generated a MHC class I tetramer RT1.A$^a$/Du51 that was labeled with phycoerythrin (PE) and allophycocyanin (APC) and stained specific populations in the spleen and graft.

Cells were first stained with a mixture of PE-conjugated and APC-conjugated RT1.A$^a$/Du51 tetramers, together with a control tetramer RT1.A$^a$/MTF-E labeled with BV421. This dual fluorochrome strategy, previously described for antigen-specific CD8$^+$ effector T cells, allows the discrimination of signal and noise staining, as specific CD8$^+$ Tregs will bind equally to each version of RT1.A$^a$/Du51 tetramer whereas random elements will not (26). Among double positive stained events, non peptide-specific cells can be visualized and excluded as they bind to a control tetramer bearing the same heavy chain RT1.A$^a$ but with an irrelevant peptide associated. Cells were secondary stained with CD8-PeCy7 and CD45RC-FITC to identify either CD8$^+$CD45RC$^{low}$ Tregs or CD8$^+$CD45RC$^{high}$ T cells. With such a strategy, we were able to identify 2.19±0.6% in the spleen and 1.16±0.25% in the graft of Du51-specific cells among CD8$^+$CD40Ig Tregs. In the naive splenic CD8$^+$CD45RC$^{low}$ Tregs population, we evaluated the precursor frequency at 0.73±0.2%, demonstrating that even 120 days following transplantation and CD40Ig treatment, the frequency was still increased around 3 times and that in naive animals, we were able to identify a pool of donor-specific Tregs. This difference was true when looking at the percentage and absolute number of tetramer-positive CD8$^+$CD40Ig Tregs or naive CD8$^+$CD45RC$^{low}$ T cells in the spleen (0.624±0.128 vs. 0.173±0.071 respectively for percentage and 623800±127700 vs. 172600±70500 for absolute number in the spleen, p<0.05). There was also significantly more Du51-specific cells among CD8$^+$CD40Ig Tregs than among CD8$^+$CD45RC$^{high}$ T cells from naive or CD40Ig-treated animals, in terms of the percentage of positive cells among each population and percentage or absolute number in the total spleen, and the percentage in the graft. There was no difference between CD8$^+$CD45RC$^{low}$ and CD8$^+$CD45RC$^{high}$ T cells from naive animals in the spleen. Interestingly, tetramer-positive cells were localized both in the graft and the spleen within the CD8$^{high}$ subset of CD8$^+$CD45RC$^{low}$ Tregs.

Altogether, these results demonstrated that we were able to generate a functional RT1A$^a$/Du51 tetramer to detect alloantigen-specific CD8$^+$ Tregs, a population that was significantly increased upon transplantation and CD40Ig treatment.

Superior Suppressive Capacity of Du51-Specific CD8$^+$CD45RC$^{low}$ Tregs Mediated by Direct and Indirect Pathways of Allorecognition and Requirement for In Vivo Tolerance Induction.

We previously demonstrated the suppressive capacity of Du51-stimulated CD8$^+$CD40Ig Tregs. In this experiment, we wanted to study the suppressive capacity of freshly sorted RT1A$^a$/Du51 tetramer-specific CD8$^+$CD40Ig Tregs (FIG. 2A). Naive CD8$^+$CD45RC$^{low}$ Tregs, total CD8$^+$CD40Ig Tregs, RT1A$^a$/Du51 tetramer negative (tet$^-$) and RT1A$^a$/Du51 tetramer positive (tet$^+$) CD8$^+$CD40Ig Tregs were sorted and incubated for 6 days with allogeneic (direct pathway) or alloantigens-loaded syngeneic pDCs (indirect pathway) and naive CFSE-labeled syngeneic CD4$^+$CD25$^-$ T cells. In this assay, RT1A$^a$/Du51 tetramer-specific CD8$^+$CD40Ig Tregs were activated by tetramer binding (data not shown and (27)). As previously described, total CD8$^+$CD40Ig Tregs suppressed more efficiently the proliferation of effector CD4$^+$CD25$^-$ T cells induced by both direct and indirect pathways of alloantigen presentation than naive CD8$^+$CD45RC$^{low}$ Tregs (FIG. 2A). Interestingly, we observed a significant difference between the suppressive potential of tcc vs. tet⁻ CD8⁺CD40Ig Tregs mediated by the direct pathway of allorecognition, with the tcc CD8⁺CD40Ig Tregs being the most potent suppressor cell subset (FIG. 2A). Although not significant but with a statistical trend (p=0.0571), the same difference was obtained regarding the indirect alloantigen presentation pathway (FIG. 2A). Moreover, suppression of CD4⁺CD25⁻ T cell proliferation was more effectively achieved by Du51-specific Tregs when induced by indirect, rather than direct, alloantigen presentation pathway. Interestingly, non-specific tet⁻ CD8⁺CD40Ig Tregs tend to be less suppressive than total CD8⁺CD40Ig Tregs, highlighting the important contribution of the Du51-specific CD8⁺ Tregs in the overall suppressive capacity of the total CD40Ig Tregs pool. These results suggested that Du51 antigen-specific CD8⁺ Tregs are the most efficient Treg subpopulation of the total CD8⁺CD40Ig Tregs pool.

To study the in vivo relevance of the differential ex vivo suppressive effect observed for Du51-specific CD8⁺CD40Ig Tregs, we performed adoptive cell transfer experiments. Total CD8⁺CD40Ig or RT1A$^a$/Du51 tetramer negative (tet⁻) CD8⁺CD40Ig Tregs, were sorted and adoptively transferred into naive grafted irradiated recipients (FIG. 2B). Unlike total CD8⁺CD40Ig Tregs, tet⁻CD8⁺CD40Ig Tregs (that were depleted in Du51 antigen-specific cells) were unable to inhibit allograft rejection, demonstrating the crucial role of the antigen-specific CD8⁺CD40Ig Tregs in the tolerogenic activity of the total CD8⁺CD40Ig Treg pool preventing allograft rejection and promoting the infectious tolerance.

Tolerance Induction by In Vivo Peptide Treatment Correlated with Increased Proportion of CD8⁺CD45RC$^{low}$ Tregs and Total Inhibition of Anti-Donor Antibody Responses.

To further determine the potential of the immunodominant peptide identified in the in vivo generation of CD8⁺ CD45RC$^{low}$ Tregs and in allograft survival, animals were separately treated using two different protocols of peptide administration with no other treatment. In the first one, animals received five intravenous (i.v) injections of 500 µg of peptide (FIG. 3A). We observed that injections of either control peptide or Du51 were not sufficient to induce a significant prolongation of allograft survival (respectively, 11 and 9.5 days, n=4) (FIG. 3A). In the second one, to improve the efficacy of the treatment, and because such small peptides are rapidly eliminated from the recipient's body, we tested mini-osmotic pumps with a constant intraperitoneal delivery of 20.8 µg of peptide per hour for 28 days, starting day-7 before transplantation. Interestingly, this protocol allowed significant prolongation of allograft survival (p<0.01 compared to control peptide and no treatment) with 25% of indefinite allograft survival using Du51 compared to control peptide (FIG. 3A). To prove that tolerance induced by peptide infusion was dependent on CD8⁺ T cells and MHC class I presentation, we co-treated recipient with peptide infusion and either a depleting anti-CD8 mAb (OX8) or a blocking anti-MHC class I mAb (OX18) (FIG. 3A) as previously described (5). Administration of both antibodies completely abolished allograft survival, indicating that recognition of MHC class I/antigen by CD8⁺ T cells was required in the establishment of tolerance obtained by peptide infusion.

Interestingly, increased dose of Du51 administered by osmotic pump delivering 41.6 µg of peptide per hour induced an indefinite allograft survival in 80% of the recipients of Lewis 1W (LEW.1W) donor hearts (FIG. 3A). However, Brown Norway (BN) third party grafts were promptly rejected at day 7 after transplantation (FIG. 3A), demonstrating that peptide Du51 infusion induces donor specific tolerance mediated by CD8⁺ Tregs.

Grafted hearts and spleens of rejecting or long-term surviving recipients treated with peptide Du51 were analyzed for signs of chronic rejection, presence of anti-donor antibodies, proportion of total and tetramer-positive CD8⁺ CD45RC$^{low}$ Tregs, and in vitro suppression towards CD4⁺ effector T cells (FIG. 3B, C, D). Anatomopathologic analysis of the graft of long-term recipients showed no signs of chronic rejection according to a previously established score (28). In addition, we observed a trend for an increase in the percentage and absolute number of total CD8⁺ T cells, in particular of CD8⁺CD45RC$^{low}$ Tregs in the spleen (FIG. 3C), as well as tetramer-positive Du51-specific Tregs (FIG. 3D) in long-term surviving peptide Du51-treated recipients compared to untreated or Du51-treated recipients that rejected their graft early. These results suggest that antigen-specific CD8⁺CD45RC$^{low}$ Tregs were induced/amplified by in vivo peptide treatment, while other subsets were not, and may be responsible of tolerance induction. We confirmed that these peptide-induced activated CD8⁺CD45RC$^{low}$ Tregs displayed suppressive activity ex vivo since they efficiently inhibit effector CD4⁺ T cell proliferation in the same manner as freshly purified CD8⁺CD40Ig Tregs. Finally, we observed a total inhibition of total IgG, IgG1, IgG2a and IgG2b alloantibodies production in long-term surviving Du51-treated recipients compared to untreated rats or Du51-treated recipients that rejected their graft early, that could correlate with the absence of chronic rejection (28) (FIG. 3B).

Infectious Tolerance Following Du51 Monotherapy.

To assess the dominant suppressive potential of induced regulatory cells involved in the long-term allograft survival generated by 1 mg/day of in vivo peptide Du51 treatment. To do so, we performed adoptive cell transfer experiments using splenocytes of long-surviving recipients into naive grafted sublethaly irradiated recipients, as we have done before (5) (FIG. 4A). First adoptive transfer of 150·10⁶ splenocytes into secondary naive grafted irradiated recipients resulted in significant prolongation of allograft survival of 50% of the recipients, demonstrating the induction of dominant regulatory cells capable to inhibit allograft rejection in newly grafted irradiated recipients. We investigated the anatomopathological status of the graft of first adoptively transferred long term splenocytes recipients and observed a complete absence of vascular lesions and obstructions (i.e. no signs of chronic rejection). Finally, we observed a total inhibition of total IgG, IgG1 and IgG2b alloantibodies production in long-term surviving first adoptively transferred recipients compared to untreated rats that displayed high alloantibodies production and comparable to naive rat, that could correlate with the absence of chronic rejection (28) (FIG. 4B).

DISCUSSION

Our current knowledge on how Tregs recognize peptides and the role of this recognition is very limited and mostly based on either transgenic mouse models using CD4⁺ Treg's TCR gene transfer (8, 11) or on murine Qa-1-restricted CD8⁺ Tregs involved in autoimmune disease and cancer and whose Qa-1-peptide repertoire has been described in the last few years (29). However, these studies suggest that antigen-specific Tregs are crucially influencing the outcome of long-term transplantation and contribute to the establishment of tolerance (30). Recent studies have characterized peptides recognized by CD8⁺ Tregs during cancer (an heme oxygenase-1-derived peptide), autoimmunity (Vβ-derived peptide) or even pregnancy (minor antigen-derived peptide) but not during transplantation (2). Transplantation is a particular setting to identify antigen recognized by Tregs as the presence of the graft is a continuous source of alloantigens and that is most certainly essential for the function and maintenance of regulatory populations and thus the survival of the grafted organ (31). The recognition of alloantigens in the context of regulation has been shown by us and others to occur mainly by the indirect pathway of presentation, and in particular supported by pDCs (6, 30, 32).

In this report, we demonstrated for the first time that $CD8^+CD45RC^{low}$ Tregs, through the indirect pathway of presentation, can recognize one dominant allopeptide, named Du51, (and one sub-dominant) derived from the β1 domain of natural donor MHC class II molecules. These peptides share 80-90% homology with human HLA class II molecules and thus could be used to detect specific $CD8^+$ Tregs in humans. By the use of a MHC-I specific tetramer, we showed that Du51-specific $CD8^+CD45RC^{low}$ Tregs were enriched in CD40Ig-treated long-term surviving recipients, expressed a biased restricted Vβ11 chain, displayed a strong suppressive activity ex-vivo and played a crucial role in tolerance induction upon adoptive transfer. Finally, peptide Du51 was shown to induce prolongation of allograft survival in vivo, inducing donor-specific $CD8^+$ Tregs.

Here, we described that the peptide Du51 displayed an unusual length of 15 aa and that shorter peptides tested failed to induce significant recognition by $CD8^+CD40Ig$ Tregs. Most of the literature has focused on short peptides (8-10 aa) bound to MHC class I, although it is known that 5-10% of peptides are longer peptides (more than 10 aa) that can be presented by MHC class I molecules (33, 34). So far, such peptides have been identified for CTL models and are mostly derived from viral antigens. To our knowledge, we provide the first description of a 15 aa peptide that can be structurally recognized by $CD8^+$ Tregs, as shown with our $RT1.A^a$/Du51 tetramers. Recent studies suggested that these long peptides drive a TCR recognition more focused on the peptide (35) and that TCRs recognize MHC class I peptides of a preferential length (36). The rat MHC class I molecule $RT1.A^a$ has been known to accommodate particularly long peptides, with key-position residues as Gln, Met or Leu at P2, Phe at P3, Pro at P4 and Arg at the C terminus (21, 22). Speir et al has demonstrated previously in a model of maternally transmitted minor histocompatibility antigen (MTF-E) of 13 residues that important anchor residues (in particular arginine at position 13 (P13)) allowed binding with considerable bulged conformation (37). We also observed that Du51 displayed an Arg at the C-term end and thus could help for $RT1.A^a$ accommodation of the peptide. Interestingly, some of the peptides that were tested by us were also tested by Ballet et al. on $CD4^+$ and $CD8^+$ T cells isolated from rejected untreated animals (including dominant peptide Du51) in the same mismatched cardiac allograft model (LEW.1W into LEW.1A) as us (18). They found two immunodominant peptides, referred by us as peptide #47 and peptide #55, all derived from LEW.1W $RT1.D^u$ molecules, involved in acute rejection of grafts from unmodified LEW.1A recipients. Importantly, peptide Du51 was not involved in acute rejection in their model and the two immunodominant peptides identified by Ballet et al. were not recognized by our $CD8^+CD40Ig$ Tregs, suggesting that Tregs and non-Tregs did not recognize the same antigens.

We were able to produce a $RT1.A^a$/Du51-tetramer, which in addition to being a valuable tool to track antigen-specific cells, can also be used to determine TCR fine specificity and affinity. With this tetramer, we identified in naive animals a pool of antigen-specific Treg precursors of 0.73%, which was expanded around three times by 120 days following transplantation and CD40Ig treatment. This precursor frequency correlated with the observations of Leavenworth et al. made in a model of arthritis in mice where they analyzed the occurrence of Qa-1-Hsp60$_{p216}$ and Qa-1.R72A-Qdm tetramer-specific $CD8^+$ Tregs and described a naive frequency of respectively ~1.65% and 0.46% of positive $CD8^+$ T cells for each (38). These observations suggest that precursor frequency of antigen specific cells in a Treg population might be higher than the frequency of a given antigen-reactive non-Treg T cells.

By the use of this MHC-I tetramer, we compared the suppressive capacity of Du51-specific and non-specific $CD8^+CD40Ig$ Tregs ex vivo in a coculture assay and in vivo through adoptive transfer of tetramer⁻ $CD8^+CD40Ig$ Tregs (depleted in tetramer⁺ $CD8^+CD40Ig$ Tregs). We demonstrated ex vivo the superior suppressive potential of tetramer⁻ over tetramer⁻ $CD8^+CD40Ig$ Tregs, which significantly inhibit $CD4^+$ effector T cells proliferation stimulated by both the direct and indirect pathways of presentation, and most efficiently in the indirect allorecognition setting. These results are in agreement with several studies demonstrating the superior suppressor potential of Tregs of indirect specificity in vitro (39, 40). In vivo, we observed a rapid allograft rejection in naive grafted irradiated recipients transferred with tetramer⁻ $CD8^+CD40Ig$ Tregs compared to recipients adoptively transferred with total $CD8^+CD40Ig$ Tregs. In a similar manner, adoptive transfer of tet⁻$CD8\alpha\alpha^+$ Tregs (depleted in tetramer Qa-1/Hsp60$_{p216}$-specific Tregs) could not prevent the development of autoimmune arthritis in a mouse model (38). Also, Tsang et al. showed a crucial role of $CD4^+$ Tregs of indirect allospecificity in transplantation tolerance, demonstrating that only adoptive transfer of TCR-transduced $CD4^+$ Tregs of both direct and indirect specificity, and not $CD4^+$ Tregs of direct specificity only, can inhibit cardiac allograft rejection (11).

We have also analyzed different markers potentially expressed by antigen-specific regulatory T cells. Foxp3 does not seem to be an interesting marker of $CD8^+CD40Ig$ Tregs unstimulated or stimulated with peptide, although upon several rounds of strong anti-CD3/anti-CD28/IL-2 stimulation, we were able to detect substantial levels of Foxp3 (data not shown). We also found increased IFNγ production and decreased IL-12 expression after peptide-specific stimulation. IFNγ was already shown by us as a crucial cytokine in our model (6).

Regarding the repertoire of induced $CD8^+CD40Ig$ Tregs, we previously showed that these cells preferentially used a TCR that recombined the Vβ11 chain and displayed a CDR3β of 9 aa in the spleen, suggesting the expansion of an oligoclonal population of Tregs (5). However, sequencing of around 700 CDR3β across six long-surviving animals demonstrated that total Vβ11⁺$CD8^+CD40Ig$ Tregs displayed a relatively diverse repertoire in the spleen. Nevertheless, a more frequent repeated sequence was found in some animals. Analysis of the TCR repertoire in the graft revealed the predominance of two TCR-Vβ chains: Vβ11 (as in the spleen) and Vβ18. Unlike the spleen, sequencing revealed biased and restricted repertoires for both chains, with some shared clonotypes for the Vβ18 TCR, as in the donor-specific blood transfusion model of induction of long-term allograft survival (41). However, the public sequence described by Douillard et al. was only found once in one animal of our study and did not represent the Vβ18-repertoire in our model. One interesting hypothesis would be that $CD8^+CD40Ig$ Tregs bearing such biased and restricted clonotypes are more potent suppressors and migrate early in the graft to exert their inhibitory activity, and then stay localized in the tolerated transplant where immune regulation is required (42). In contrast, total $CD8^+CD40Ig$ Tregs that reside in the spleen but displayed a non (Vβ18) or less (Vβ11) restricted repertoire (and consequently closer to the naive Tregs' repertoire) potentially identify distinct regulatory populations (that possibly do not express the same chemokine receptors) being recruited upon subsequent inflammation. Despite some shared clonotypes for both Vβ11 and Vβ18 (Suppl. Table 1), we could not find public CDR3 sequences. Analyzing more precisely the repertoire of antigen-specific CD8+CD40Ig Tregs in the spleen by focusing on tetramer Du51+ Tregs, we demonstrated reduced clonotypic diversity of Du51-specific Vβ11+CD8+CD40Ig Tregs (compared to the total CD8+CD40Ig Tregs from naive and CD40Ig-treated spleen and similar to the graft CD8+ CD40Ig Tregs), but not of Du51-specific Vβ18+CD8+ CD40Ig Tregs. Thus, the Vβ18 chain usage might not be optimal for recognition of this particular antigen. However, even this analysis of the antigen-specific population did not reveal public clonotypes for this Treg population. TCR sequences that are shared between individuals tend to be more efficiently produced by a process of convergent recombination (43) and thus present at a higher frequency in the naive T cell repertoire (44-46). However, inter-individually shared TCR sequences are not necessarily dominant in the immune response to antigen (47). This appears to be the case in our model, suggesting that this process may be modified by either TCR expansion or TCRα-chain pairing. More recent publications have revealed the important contribution of the alpha-chain in the specific pMHC recognition and how TCRαβ diversity should be taken into consideration, as some specific TCR Vα pairings dictate and alter MHC restriction (48, 49). In the literature, a consensus on TCR diversity of naive CD4+ Tregs was obtained stating that more is better. Authors demonstrated that a high TCR diversity ensures optimal Treg expansion and function by increasing the probability of having antigen-specific clones responding (13, 16, 50, 51). In our model, naive CD8+ Tregs displayed a highly diverse repertoire that was remodeled and biased by expansion of Du51-specific CD8+ Tregs after transplantation and CD40Ig treatment.

At last, from a therapeutic point of view, the identification of natural peptide recognized by regulatory T cells in transplantation is an important goal as new strategies using amplified CD4+ Tregs are being tested currently in human transplantation (30, 52). The difficulty is that these human CD4+ Tregs amplified in a polyclonal way by non-specific stimulus such as anti-CD3/CD28 antibodies are less efficient than antigen-specific Tregs (2, 53), display limited expansion capacity and are usually outgrown by conventional effector T cells (54). The use of specific antigen to expand Tregs in short-term culture would surely improve clinical settings. As a proof of principle, we administered the dominant peptide Du51 in naive grafted recipients, without immunosuppressive treatment, and observed significant prolongation of allograft survival. This is the first time this extended survival can be obtained with allopeptide alone (i.e. without immunosuppressive drugs) in rodents and clearly demonstrates both the efficiency of this peptide and the implication of the indirect pathway of presentation in tolerance induction. Some studies had described earlier immunomodulatory effects of HLA-derived peptides on alloimmune responses (55). Especially, an HLA-B7 derived-peptide, called Allotrap, was shown to prolong skin and heart allograft survival when associated with ciclosporin administration in mice and rat respectively (56, 57). Its effect was associated with modulation of heme-oxygenase 1 activity (58). In our model, administration of either anti-CD8 or anti-MHC-I antibodies in combination with peptide Du51 completely abolished allograft survival. Thus, the in vivo therapeutic effect obtained with peptide Du51 infusion was directly linked to MHC class I presentation and CD8+ T cell induction. Moreover, the immunodominant peptide Du51 induced a donor-specific inhibition of alloimmune responses as third party grafts were promptly rejected. In addition, the peptide Du51-induced allograft survival was accompanied by a total inhibition of anti-donor antibodies that is probably related to the occurrence of antigen-specific CD8+ Tregs after infusion of the allopeptide. This result is important as it shows the potency of peptide-induced Tregs to inhibit acute and chronic allograft rejection occurrence, and opens new possibilities in human transplantation. In addition, such expanded highly suppressive Tregs could provide us with more fundamental information on new and poorly described genes overexpressed with such conditions and that could be used as biomarkers (6). Finally, we could assume that the presence of this CD8+CD45RC$^{low}$ Treg population in some groups of patients could be associated with a better prognosis during the course of diseases (59, 60).

In conclusion, our study indicates that MHC class II donor antigen can be used to boost antigen-specific CD8+ Treg generation and/or function, and that in turn, these Tregs inhibit anti-donor immune responses allowing the establishment of a true tolerance. We also demonstrated that antigen-specific CD8+ Tregs' TCRs display a private and restricted repertoire that ensures efficient expansion and suppression of alloreactive immune responses. Altogether, these results highlight the importance of the TCR, of its interaction with MHC/peptide and open new possibilities in the generation of this population that could be transferrable to human settings.

REFERENCES

Throughout this application, various references describe the state of the art to which this invention pertains. The disclosures of these references are hereby incorporated by reference into the present disclosure.

1. Bluestone, J. A., Auchincloss, H., Nepom, G. T., Rotrosen, D., St Clair, E. W., and Turka, L. A. 2010. The Immune Tolerance Network at 10 years: tolerance research at the bedside. *Nat Rev Immunol* 10:797-803.
2. Guillonneau, C., Picarda, E., and Anegon, I. 2010. CD8+ regulatory T cells in solid organ transplantation. *Curr Opin Organ Transplant* 15:751-756.
3. Li, X. L., Menoret, S., Le Mauff, B., Angin, M., and Anegon, I. 2008. Promises and obstacles for the blockade of CD40-CD40L interactions in allotransplantation. *Transplantation* 86:10-15.
4. Guillot, C., Guillonneau, C., Mathieu, P., Gerdes, C. A., Menoret, S., Braudeau, C., Tesson, L., Renaudin, K., Castro, M. G., Lowenstein, P. R., et al. 2002. Prolonged blockade of CD40-CD40 ligand interactions by gene transfer of CD40Ig results in long-term heart allograft survival and donor-specific hyporesponsiveness, but does not prevent chronic rejection. *J Immunol* 168:1600-1609.
5. Guillonneau, C., Hill, M., Hubert, F. X., Chiffoleau, E., Herve, C., Li, X. L., Heslan, M., Usal, C., Tesson, L., Menoret, S., et al. 2007. CD40Ig treatment results in allograft acceptance mediated by CD8CD45RC T cells, IFN-gamma, and indoleamine 2,3-dioxygenase. *J Clin Invest* 117:1096-1106.
6. Li, X. L., Menoret, S., Bezie, S., Caron, L., Chabannes, D., Hill, M., Halary, F., Angin, M., Heslan, M., Usal, C., et al. 2010. Mechanism and localization of CD8 regulatory T cells in a heart transplant model of tolerance. *J Immunol* 185:823-833.
7. Picarda, E., Anegon, I., and Guillonneau, C. 2011. T-cell receptor specificity of CD8(+) Tregs in allotransplantation. *Immunotherapy* 3:35-37.

8. Tsang, J. Y., Ratnasothy, K., Li, D., Chen, Y., Bucy, R. P., Lau, K. F., Smyth, L., Lombardi, G., Lechler, R., and Tam, P. K. 2011. The potency of allospecific Tregs cells appears to correlate with T cell receptor functional avidity. *Am J Transplant* 11:1610-1620.
9. Joffre, O., Santolaria, T., Calise, D., Al Saati, T., Hudrisier, D., Romagnoli, P., and van Meerwijk, J. P. 2008. Prevention of acute and chronic allograft rejection with CD4+ CD25+Foxp3+ regulatory T lymphocytes. *Nat Med* 14:88-92.
10. Tang, Q., Henriksen, K. J., Bi, M., Finger, E. B., Szot, G., Ye, J., Masteller, E. L., McDevitt, H., Bonyhadi, M., and Bluestone, J. A. 2004. In vitro-expanded antigen-specific regulatory T cells suppress autoimmune diabetes. *J Exp Med* 199:1455-1465.
11. Tsang, J. Y., Tanriver, Y., Jiang, S., Xue, S. A., Ratnasothy, K., Chen, D., Stauss, H. J., Bucy, R. P., Lombardi, G., and Lechler, R. 2008. Conferring indirect allospecificity on CD4+CD25+ Tregs by TCR gene transfer favors transplantation tolerance in mice. *J Clin Invest* 118:3619-3628.
12. Sagoo, P., Aft, N., Garg, G., Nestle, F. O., Lechler, R. I., and Lombardi, G. 2011. Human regulatory T cells with alloantigen specificity are more potent inhibitors of alloimmune skin graft damage than polyclonal regulatory T cells. *Sci Transl Med* 3:83ra42.
13. Wing, J. B., and Sakaguchi, S. 2011. TCR diversity and Treg cells, sometimes more is more. *Eur J Immunol* 41:3097-3100.
14. Masteller, E. L., Tang, Q., and Bluestone, J. A. 2006. Antigen-specific regulatory T cells—ex vivo expansion and therapeutic potential. *Semin Immunol* 18:103-110.
15. Ohkura, N., and Sakaguchi, S. 2010. Regulatory T cells: roles of T cell receptor for their development and function. *Semin Immunopathol* 32:95-106.
16. Fohse, L., Suffner, J., Suhre, K., Wahl, B., Lindner, C., Lee, C. W., Schmitz, S., Haas, J. D., Lamprecht, S., Koenecke, C., et al. 2011. High TCR diversity ensures optimal function and homeostasis of Foxp3+ regulatory T cells. *Eur J Immunol* 41:3101-3113.
17. van Denderen, B., Peche, H., Gagne, K., Usal, C., Cuturi, M. C., and Soulillou, J. P. 2001. Identification of immunodominant donor MHC peptides following rejection and donor strain transfusion-induced tolerance of heart allografts in adult rats. *Eur J Immunol* 31:1333-1339.
18. Ballet, C., Renaudin, K., Degauque, N., Le Mai, H., Boëffard, F., Lair, D., Berthelot, L., Feng, C., Smit, H., Usal, C., et al. 2008. Indirect CD4+TH1 response, anti-donor antibodies and diffuse C4d graft deposits in long term recipients conditioned by donor antigens priming. *Am J Transplant* 9:697-708.
19. Ettinger, R. A., Moustakas, A. K., and Lobaton, S. D. 2004. Open reading frame sequencing and structure-based alignment of polypeptides encoded by RT1-Bb, RT1-Ba, RT1-Db, and RT1-Da alleles. *Immunogenetics* 56:585-596.
20. Thorpe, C. J., Moss, D. S., Powis, S. J., Howard, J. C., Butcher, G. W., and Travers, P. J. 1995. An analysis of the antigen binding site of RT1.Aa suggests an allele-specific motif. *Immunogenetics* 41:329-331.
21. Powis, S. J., Young, L. L., Joly, E., Barker, P. J., Richardson, L., Brandt, R. P., Melief, C. J., Howard, J. C., and Butcher, G. W. 1996. The rat cim effect: TAP allele-dependent changes in a class I MHC anchor motif and evidence against C-terminal trimming of peptides in the ER. *Immunity* 4:159-165.
22. Stevens, J., Wiesmuller, K. H., Barker, P. J., Walden, P., Butcher, G. W., and Joly, E. 1998. Efficient generation of major histocompatibility complex class I-peptide complexes using synthetic peptide libraries. *J Biol Chem* 273:2874-2884.
23. Stevens, J., Wiesmuller, K. H., Walden, P., and Joly, E. 1998. Peptide length preferences for rat and mouse MHC class I molecules using random peptide libraries. *Eur J Immunol* 28:1272-1279.
24. Karim, M., Feng, G., Wood, K. J., and Bushell, A. R. 2005. CD25+CD4+ regulatory T cells generated by exposure to a model protein antigen prevent allograft rejection: antigen-specific reactivation in vivo is critical for bystander regulation. *Blood* 105:4871-4877.
25. Wan, Q., Kozhaya, L., Imberg, K., Mercer, F., Zhong, S., Krogsgaard, M., and Unutmaz, D. 2013. Probing the effector and suppressive functions of human T cell subsets using antigen-specific engineered T cell receptors. *PLoS One* 8:e56302.
26. Chattopadhyay, P. K., Melenhorst, J. J., Ladell, K., Gostick, E., Scheinberg, P., Barrett, A. J., Wooldridge, L., Roederer, M., Sewell, A. K., and Price, D. A. 2008. Techniques to improve the direct ex vivo detection of low frequency antigen-specific $CD8^+$ T cells with peptide-major histocompatibility complex class I tetramers. *Cytometry A* 73:1001-1009.
27. Wooldridge, L., Lissina, A., Cole, D. K., van den Berg, H. A., Price, D. A., and Sewell, A. K. 2009. Tricks with tetramers: how to get the most from multimeric peptide-MHC. *Immunology* 126:147-164.
28. Guillonneau, C., Seveno, C., Dugast, A. S., Li, X. L., Renaudin, K., Haspot, F., Usal, C., Veziers, J., Anegon, I., and Vanhove, B. 2007. Anti-CD28 antibodies modify regulatory mechanisms and reinforce tolerance in CD40Ig-treated heart allograft recipients. *J Immunol* 179:8164-8171.
29. Kim, H. J., and Cantor, H. 2011. Regulation of self-tolerance by Qa-1-restricted CD8(+) regulatory T cells. *Semin Immunol* 23:446-452.
30. Wood, K. J., Bushell, A., and Hester, J. 2012. Regulatory immune cells in transplantation. *Nat Rev Immunol* 12:417-430.
31. Hamano, K., Rawsthorne, M. A., Bushell, A. R., Morris, P. J., and Wood, K. J. 1996. Evidence that the continued presence of the organ graft and not peripheral donor microchimerism is essential for maintenance of tolerance to alloantigen in vivo in anti-CD4 treated recipients. *Transplantation* 62:856-860.
32. Gokmen, M. R., Lombardi, G., and Lechler, R. I. 2008. The importance of the indirect pathway of allorecognition in clinical transplantation. *Curr Opin Immunol* 20:568-574.
33. Burrows, S. R., Rossjohn, J., and McCluskey, J. 2006. Have we cut ourselves too short in mapping CTL epitopes? *Trends Immunol* 27:11-16.
34. Hickman, H. D., Luis, A. D., Buchli, R., Few, S. R., Sathiamurthy, M., VanGundy, R. S., Giberson, C. F., and Hildebrand, W. H. 2004. Toward a definition of self: proteomic evaluation of the class I peptide repertoire. *J Immunol* 172:2944-2952.
35. Liu, Y. C., Chen, Z., Burrows, S. R., Purcell, A. W., McCluskey, J., Rossjohn, J., and Gras, S. 2012. The energetic basis underpinning T-cell receptor recognition of a super-bulged peptide bound to a major histocompatibility complex class I molecule. *J Biol Chem* 287:12267-12276.

36. Ekeruche-Makinde, J., Miles, J. J., van den Berg, H. A., Skowera, A., Cole, D. K., Dolton, G., Schauenburg, A. J., Tan, M. P., Pentier, J. M., Llewellyn-Lacey, S., et al. 2013. Peptide length determines the outcome of TCR/peptide-MHCI engagement. *Blood* 121:1112-1123.

37. Speir, J. A., Stevens, J., Joly, E., Butcher, G. W., and Wilson, I. A. 2001. Two different, highly exposed, bulged structures for an unusually long peptide bound to rat MHC class I RT1-Aa. *Immunity* 14:81-92.

38. Leavenworth, J. W., Tang, X., Kim, H. J., Wang, X., and Cantor, H. 2013. Amelioration of arthritis through mobilization of peptide-specific CD8+ regulatory T cells. *J Clin Invest* 123:1382-1389.

39. Hara, M., Kingsley, C. I., Niimi, M., Read, S., Turvey, S. E., Bushell, A. R., Morris, P. J., Powrie, F., and Wood, K. J. 2001. IL-10 is required for regulatory T cells to mediate tolerance to alloantigens in vivo. *J Immunol* 166:3789-3796.

40. Jiang, S., Tsang, J., Game, D. S., Stevenson, S., Lombardi, G., and Lechler, R. I. 2006. Generation and expansion of human CD4+CD25+ regulatory T cells with indirect allospecificity: Potential reagents to promote donor-specific transplantation tolerance. *Transplantation* 82:1738-1743.

41. Douillard, P., Pannetier, C., Josien, R., Menoret, S., Kourilsky, P., Soulillou, J. P., and Cuturi, M. C. 1996. Donor-specific blood transfusion-induced tolerance in adult rats with a dominant TCR-Vbeta rearrangement in heart allografts. *J Immunol* 157:1250-1260.

42. Hayashi, Y., Tsukumo, S., Shiota, H., Kishihara, K., and Yasutomo, K. 2004. Antigen-specific T cell repertoire modification of CD4+CD25+ regulatory T cells. *J Immunol* 172:5240-5248.

43. Venturi, V., Price, D. A., Douek, D. C., and Davenport, M. P. 2008. The molecular basis for public T-cell responses? *Nat Rev Immunol* 8:231-238.

44. Quigley, M. F., Greenaway, H. Y., Venturi, V., Lindsay, R., Quinn, K. M., Seder, R. A., Douek, D. C., Davenport, M. P., and Price, D. A. 2010. Convergent recombination shapes the clonotypic landscape of the naive T-cell repertoire. *Proc Natl Acad Sci USA* 107:19414-19419.

45. Robins, H. S., Srivastava, S. K., Campregher, P. V., Turtle, C. J., Andriesen, J., Riddell, S. R., Carlson, C. S., and Warren, E. H. 2010. Overlap and effective size of the human CD8+ T cell receptor repertoire. *Sci Transl Med* 2:47ra64.

46. Venturi, V., Quigley, M. F., Greenaway, H. Y., Ng, P. C., Ende, Z. S., McIntosh, T., Asher, T. E., Almeida, J. R., Levy, S., Price, D. A., et al. 2011. A mechanism for TCR sharing between T cell subsets and individuals revealed by pyrosequencing. *J Immunol* 186:4285-4294.

47. Thomas, P. G., Handel, A., Doherty, P. C., and La Gruta, N. L. 2013. Ecological analysis of antigen-specific CTL repertoires defines the relationship between naive and immune T-cell populations. *Proc Natl Acad Sci USA* 110:1839-1844.

48. Day, E. B., Guillonneau, C., Gras, S., La Gruta, N. L., Vignali, D. A., Doherty, P. C., Purcell, A. W., Rossjohn, J., and Turner, S. J. 2011. Structural basis for enabling T-cell receptor diversity within biased virus-specific CD8+ T-cell responses. *Proc Natl Acad Sci USA* 108:9536-9541.

49. Turner, S. J., and Rossjohn, J. 2011. alphabeta T cell receptors come out swinging. *Immunity* 35:660-662.

50. Haribhai, D., Williams, J. B., Jia, S., Nickerson, D., Schmitt, E. G., Edwards, B., Ziegelbauer, J., Yassai, M., Li, S. H., Relland, L. M., et al. 2011. A requisite role for induced regulatory T cells in tolerance based on expanding antigen receptor diversity. *Immunity* 35:109-122.

51. Adeegbe, D., Matsutani, T., Yang, J., Altman, N. H., and Malek, T. R. 2010. CD4(+) CD25(+) Foxp3(+) T regulatory cells with limited TCR diversity in control of autoimmunity. *J Immunol* 184:56-66.

52. Safinia, N., Leech, J., Hernandez-Fuentes, M., Lechler, R., and Lombardi, G. 2013. Promoting transplantation tolerance; adoptive regulatory T cell therapy. *Clin Exp Immunol* 172:158-168.

53. Renner, P., Popp, F. C., Eggenhofer, E., Slowik, P., Piso, P., Geissler, E. K., Schlitt, H. J., and Dahlke, M. H. 2010. Antigen-specific recognition is critical for the function of regulatory CD8(+)CD28(−) T cells. *Transpl Immunol* 22:144-149.

54. Tang, Q., Bluestone, J. A., and Kang, S. M. 2012. CD4(+)Foxp3(+) regulatory T cell therapy in transplantation. *J Mol Cell Riot* 4:11-21.

55. Zang, W., and Murphy, B. 2005. Peptide-mediated immunosuppression. *Am J Ther* 12:592-599.

56. Buelow, R., Veyron, P., Clayberger, C., Pouletty, P., and Touraine, J. L. 1995. Prolongation of skin allograft survival in mice following administration of ALLOTRAP. *Transplantation* 59:455-460.

57. Murphy, B., Kim, K. S., Buelow, R., Sayegh, M. H., and Hancock, W. W. 1997. Synthetic MHC class I peptide prolongs cardiac survival and attenuates transplant arteriosclerosis in the Lewis→Fischer 344 model of chronic allograft rejection. *Transplantation* 64:14-19.

58. Iyer, S., Woo, J., Cornejo, M. C., Gao, L., McCoubrey, W., Maines, M., and Buelow, R. 1998. Characterization and biological significance of immunosuppressive peptide D2702.75-84(E→V) binding protein. Isolation of heme oxygenase-1. *J Biol Chem* 273:2692-2697.

59. Ordonez, L., Bernard, I., L'Faqihi-Olive, F. E., Tervaert, J. W., Damoiseaux, J., and Saoudi, A. 2009. CD45RC isoform expression identifies functionally distinct T cell subsets differentially distributed between healthy individuals and AAV patients. *PLoS One* 4:e5287.

60. Ordonez, L., Bernard, I., Chabod, M., Augusto, J. F., Lauwers-Cances, V., Cristini, C., Cuturi, M. C., Subra, J. F., and Saoudi, A. 2013. A higher risk of acute rejection of human kidney allografts can be predicted from the level of CD45RC expressed by the recipients' CD8 T cells. *PLoS One* 8:e69791.

61. Garboczi, D. N., Hung, D. T., and Wiley, D. C. 1992. HLA-A2-peptide complexes: refolding and crystallization of molecules expressed in *Escherichia coli* and complexed with single antigenic peptides. *Proc Natl Acad Sci USA* 89:3429-3433.

62. Venturi, V., Kedzierska, K., Turner, S. J., Doherty, P. C., and Davenport, M. P. 2007. Methods for comparing the diversity of samples of the T cell receptor repertoire. *J Immunol Methods* 321:182-195.

63. Guillonneau, C., Louvet, C., Renaudin, K., Heslan, J. M., Heslan, M., Tesson, L., Vignes, C., Guillot, C., Choi, Y., Turka, L. A., et al. 2004. The role of TNF-related activation-induced cytokine-receptor activating NF-kappa B interaction in acute allograft rejection and CD40L-independent chronic allograft rejection. *J Immunol* 172:1619-1629.

64. Gras S, Kjer-Nielsen L, Burrows S R, McCluskey J, Rossjohn J. 2008. T-cell receptor bias and immunity. *Curr Opin Immunol.* 20(1):119-25.

The invention claimed is:

1. An isolated peptide derived from a MHC class II molecule, wherein the isolated peptide has a length of from 15 to 40 amino acids, and wherein the isolated peptide has an amino acid sequence REEYARFDSDVGEYR (SEQ ID NO: 1) or comprises the amino acid sequence: REEYARFDSDVGEYR (SEQ ID NO: 1), or comprises a variant of SEQ ID NO:1 selected from the group consisting of: REEYARFDSDVGEFR (SEQ ID NO: 3), REEYVRFDSDVGEYR (SEQ ID NO: 4), QEEYARFDSDVGEYR (SEQ ID NO: 5), REEYARFDSDVGVYR (SEQ ID NO: 6), NREEYARFDSDVGEFR (SEQ ID NO: 7), NREEYVRFDSDVGEYR (SEQ ID NO: 8), NQEEYARFDSDVGEYR (SEQ ID NO: 9) and NREEYAREDSDVGVYR (SEQ ID NO: 10), with the caveat that the isolated peptide is not NREEYARFDSDVGEYR (SEQ ID NO: 2).

2. The isolated peptide according to claim 1, wherein the isolated peptide is 16 amino acids in length.

3. A nucleic acid sequence encoding the peptide of claim 1.

4. A vector comprising the nucleic acid sequence of claim 3.

5. A host cell comprising the vector of claim 4.

6. A MHC/peptide multimer comprising
a peptide sequence encoding multiple peptides, wherein at least one encoded peptide is derived from a MHC class II molecule and has a length of from 15 to 25 amino acids, and wherein the at least one encoded peptide has an amino acid sequence REEYARFDSDVGEYR (SEQ ID NO: 1) or comprises the amino acid sequence: REEYARFDSDVGEYR (SEQ ID NO: 1), or comprises a variant thereof, selected from the group consisting of:

NREEYARFDSDVGEYR, (SEQ ID NO: 2)

REEYARFDSDVGEFR; (SEQ ID NO: 3)

REEYVRFDSDVGEYR; (SEQ ID NO: 4)

QEEYARFDSDVGEYR; (SEQ ID NO: 5)

REEYARFDSDVGVYR; (SEQ ID NO: 6)

NREEYARFDSDVGEFR; (SEQ ID NO: 7)

NREEYVRFDSDVGEYR; (SEQ ID NO: 8)

NQEEYARFDSDVGEYR; (SEQ ID NO: 9)
or

NREEYARFDSDVGVYR. (SEQ ID NO: 10)

7. In vitro or ex vivo method for generating a population of CD8+CD45RC$^{low}$ Tregs, comprising a step of culturing a population of CD8+ Tregs with a culture medium comprising
i) an isolated peptide derived from a MHC class II molecule, wherein the isolated peptide has a length of from 15 to 25 amino acids, and wherein the isolated peptide has an amino acid sequence REEYARFDSDVGEYR (SEQ ID NO: 1) or comprises the amino acid sequence: REEYARFDSDVGEYR (SEQ ID NO: 1) or
ii) comprises a variant of SEQ ID NO: 1 selected from the group consisting of: NREEYARFDSDVGEYR (SEQ ID NO: 2); REEYARFDSDVGEFR (SEQ ID NO: 3): REEYVRFDSDVGEYR (SEQ ID NO: 4); QEEYARFDSDVGEYR (SEQ ID NO: 5); REEYARFDSDVGVYR (SEQ ID NO: 6); NREEYARFDSDVGEFR (SEQ ID NO: 7); NREEYVRFDSDVGEYR (SEQ ID NO: 8); NQEEYARFDSDVGEYR (SEQ. ID NO: 9) and NREEYARFDSDVGVYR (SEQ ID NO: 10), wherein the step of culturing is performed in the presence of a population of plasmacytoid dendritic cells.

8. An in vitro or ex vivo method for generating a population of CD8±CD45RC$^{1''}$ Tregs, comprising a step of
culturing a population of CD8+ Tregs with a culture medium comprising a MHC/peptide multimer comprising
i) a peptide derived from a MHC class II molecule, wherein the peptide has a length of from 15 to 25 amino acids, and wherein the peptide has an amino acid sequence REEYARFDSDVGEYR (SEQ ID NO: 1) or comprises the amino acid sequence: REEYARFDSDVGEYR (SEQ ID NO: 1), or
ii) a variant of SEQ ID NO:1 selected from the group consisting of:

NREEYARFDSDVGEYR, (SEQ ID NO: 2)

REEYARFDSDVGEFR; (SEQ ID NO: 3)

REEYVRFDSDVGEYR; (SEQ ID NO: 4)

QEEYARFDSDVGEYR; (SEQ ID NO: 5)

REEYARFDSDVGVYR; (SEQ ID NO: 6)

NREEYARFDSDVGEFR; (SEQ ID NO: 7)

NREEYVRFDSDVGEYR; (SEQ ID NO: 8)

NQEEYARFDSDVGEYR; (SEQ ID NO: 9)
or

NREEYARFDSDVGVYR. (SEQ ID NO: 10)

9. A method of inducing tolerance in a patient in need thereof, comprising
administering to the patient a therapeutically effective amount of
i) a peptide derived from a MHC class II molecule, wherein the peptide has a length of from 15 to 25 amino acids, and wherein the peptide has an amino acid sequence REEYARFDSDVGEYR (SEQ ID NO: 1) or comprises the amino acid sequence: REEYARFDSDVGEYR (SEQ ID NO: 1); or
ii) comprises a variant of SEQ ID NO:1 selected from the group consisting of:

NREEYARFDSDVGEYR, (SEQ ID NO: 2)

REEYARFDSDVGEFR, (SEQ ID NO: 3)

REEYVRFDSDVGEYR, (SEQ ID NO: 4)

QEEYARFDSDVGEYR, (SEQ ID NO: 5)

-continued

```
                          (SEQ ID NO: 6)
REEYARFDSDVGVYR, (SEQ ID NO: 7)
NREEYARFDSDVGEFR, (SEQ ID NO: 8)
NREEYVRFDSDVGEYR, (SEQ ID NO: 9)
NQEEYARFDSDVGEYR
and (SEQ ID NO: 10)
NREEYARFDSDVGVYR;
or
``` iii) comprises a multimer comprising the peptide or the variant of the peptide.

10. A method of preventing or reducing transplant rejection in a patient in need thereof in a patient in need thereof, comprising administering to the patient a therapeutically effective amount of i) a peptide derived from a MHC class II molecule, wherein the peptide has a length of from 15 to 25 amino acids, and wherein the peptide has an amino acid sequence REEYARFDSDVGEYR (SEQ ID NO: 1) or comprises the amino acid sequence: REEYARFDSDVGEYR (SEQ ID NO: 1);

ii) comprises a variant of SEQ ID NO:1 selected from the group consisting of:

```
                          (SEQ ID NO: 2)
NREEYARFDSDVGEYR, (SEQ ID NO: 3)
REEYARFDSDVGEFR, (SEQ ID NO: 4)
REEYVRFDSDVGEYR, (SEQ ID NO: 5)
QEEYARFDSDVGEYR, (SEQ ID NO: 6)
REEYARFDSDVGVYR, (SEQ ID NO: 7)
NREEYARFDSDVGEFR, (SEQ ID NO: 8)
NREEYVRFDSDVGEYR, (SEQ ID NO: 9)
NQEEYARFDSDVGEYR
and (SEQ ID NO: 10)
NREEYARFDSDVGVYR;
or
``` iii) a multimer comprising the peptide or the variant of the peptide.

11. A pharmaceutical composition comprising a) a peptide of length of from 15 to 40 amino acids which is derived from a MHC class II molecule, wherein the peptide comprises an amino acid sequence: REEYARFDSDVGEYR (SEQ ID NO: 1) or a variant thereof, selected from the group consisting of:

```
                          (SEQ ID NO: 3)
REEYARFDSDVGEFR, (SEQ ID NO: 4)
REEYVRFDSDVGEYR, (SEQ ID NO: 5)
QEEYARFDSDVGEYR, (SEQ ID NO: 6)
REEYARFDSDVGVYR, (SEQ ID NO: 7)
NREEYARFDSDVGEFR, (SEQ ID NO: 8)
NREEYVRFDSDVGEYR, (SEQ ID NO: 9)
NQEEYARFDSDVGEYR
and (SEQ ID NO: 10)
NREEYARFDSDVGVYR;
``` or b) a nucleic acid encoding the peptide; or c) an expression vector comprising the nucleic acid; or d) a host cell comprising the expression vector; or e) a MHC/peptide multimer comprising the peptide; or f) an antigen-presenting cell comprising a complex comprising an MHC molecule and the peptide;

and a pharmaceutically acceptable carrier.

12. An in vitro method for determining whether a transplanted patient is tolerant, comprising a step of determining the presence of CD8+CD45RClow Tregs in a biological sample obtained from said transplanted patient, by contacting said biological sample with a binding partner capable of selectively interacting with CD8+CD45RClow Tregs, wherein the binding partner is a MHC/peptide multimer comprising i) a peptide derived from a MHC class II molecule, wherein the peptide has a length of from 15 to 25 amino acids, and wherein the peptide has an amino acid sequence REEYARFDSDVGEYR (SEQ ID NO: 1) or comprises the amino acid sequence: REEYARFDSDVGEYR (SEQ ID NO: 1), or ii) a variant of SEQ ID NO:1 selected from the group consisting of:

```
                          (SEQ ID NO: 2)
NREEYARFDSDVGEYR, (SEQ ID NO: 3)
REEYARFDSDVGEFR, (SEQ ID NO: 4)
REEYVRFDSDVGEYR, (SEQ ID NO: 5)
QEEYARFDSDVGEYR, (SEQ ID NO: 6)
REEYARFDSDVGVYR, (SEQ ID NO: 7)
NREEYARFDSDVGEFR, (SEQ ID NO: 8)
NREEYVRFDSDVGEYR,
```

-continued

```
                        (SEQ ID NO: 9)
NQEEYARFDSDVGEYR
and (SEQ ID NO: 10)
NREEYARFDSDVGVYR;
``` wherein the presence of CD8+CD45RClow Tregs is indicative of tolerance.

* * * * *